United States Patent
Ii et al.

(10) Patent No.: US 6,383,175 B1
(45) Date of Patent: May 7, 2002

(54) MEDICAL LASER APPARATUS AND DIAGNOSTIC/TREATMENT APPARATUS USING THE MEDICAL LASER APPARATUS

(75) Inventors: Yoshiteru Ii; Akira Kaneda, both of Osaka-fu; Takayoshi Yuzu, Nara-ken; Toshiyoshi Yamamoto, Hyogo-ken; Harubumi Kato, Tokyo-to; Katsuo Aizawa, Kanagawa-ken, all of (JP)

(73) Assignee: Matsushita Electric Industrial Co., Ltd., Osaka (JP)

(*) Notice: Subject to any disclaimer, the term of this patent is extended or adjusted under 35 U.S.C. 154(b) by 0 days.

(21) Appl. No.: 09/406,734

(22) Filed: Sep. 28, 1999

Related U.S. Application Data

(60) Division of application No. 08/545,101, filed on Oct. 19, 1995, now Pat. No. 6,214,033, which is a continuation-in-part of application No. 08/174,370, filed on Dec. 28, 1993, now abandoned.

(30) Foreign Application Priority Data

Dec. 28, 1992 (JP) .............................. 4-347784
Aug. 24, 1993 (JP) .............................. 5-209325

(51) Int. Cl.$^7$ ........................... A61B 18/22; A61B 18/24
(52) U.S. Cl. ............................... 606/3; 606/10; 606/13; 606/15; 607/89
(58) Field of Search ........... 606/2, 3–13; 351/206–212; 607/88, 89

(56) References Cited

U.S. PATENT DOCUMENTS

| | | |
|---|---|---|
| 3,534,289 A | 10/1970 | Clark et al. |
| 4,336,809 A | 6/1982 | Clark |
| 4,509,130 A | 4/1985 | Menzies et al. |
| 4,556,057 A | 12/1985 | Hiruma et al. |
| 4,644,948 A | 2/1987 | Lang et al. |
| 4,702,245 A | 10/1987 | Schroder et al. |
| 4,932,934 A | 6/1990 | Dougherty et al. |
| 4,994,059 A | 2/1991 | Kosa et al. |
| 5,030,200 A | 7/1991 | Judy et al. |
| 5,272,716 A | 12/1993 | Soltz et al. |
| 5,412,674 A | * 5/1995 | Scheps ........................ 372/22 |

FOREIGN PATENT DOCUMENTS

| | | |
|---|---|---|
| EP | 0429297 | 5/1991 |
| GB | 2007015 | 5/1979 |
| JP | 58-64307 | 4/1983 |
| JP | 61-56663 | 3/1986 |
| JP | 63-2633 | 1/1988 |
| JP | 63-9464 | 2/1988 |
| JP | 4/347784 | 12/1992 |
| JP | 6/246014 | 9/1994 |
| JP | 7/100218 | 4/1995 |
| WO | WO9404665 | 12/1994 |

* cited by examiner

Primary Examiner—David M. Shay
(74) Attorney, Agent, or Firm—Wenderoth, Lind & Ponack, L.L.P.

(57) ABSTRACT

In photodynamic diagnosis and photodynamic therapy, the oscillating wavelength of laser light from a light source is fitted to a plurality of different kinds of photosensitizers and exciting conditions thereof. Moreover, diagnosis and treatment are achieved using a single light source. Concurrent diagnosis during treatment is realized as well. A semiconductor laser generates laser light having an oscillating wavelength which is variable and a full width at half maximum which is narrow. A light transmission line guides an irradiated laser light the vicinity of a focus, an image transmission line observes the focus and the periphery thereof, a fluorescence light extracting device extracts only the fluorescence light emitted from a photosensitizer excited by the irradiated laser light, an image-pick-up/analyzing device picks up and analyzes an image of the extracted fluorescence light and an image display device displays the analyzing result.

6 Claims, 12 Drawing Sheets

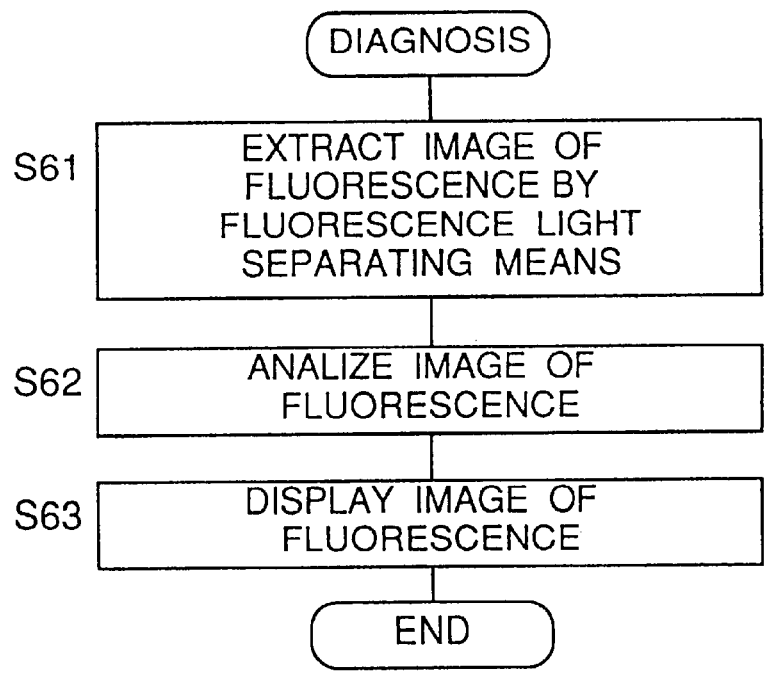
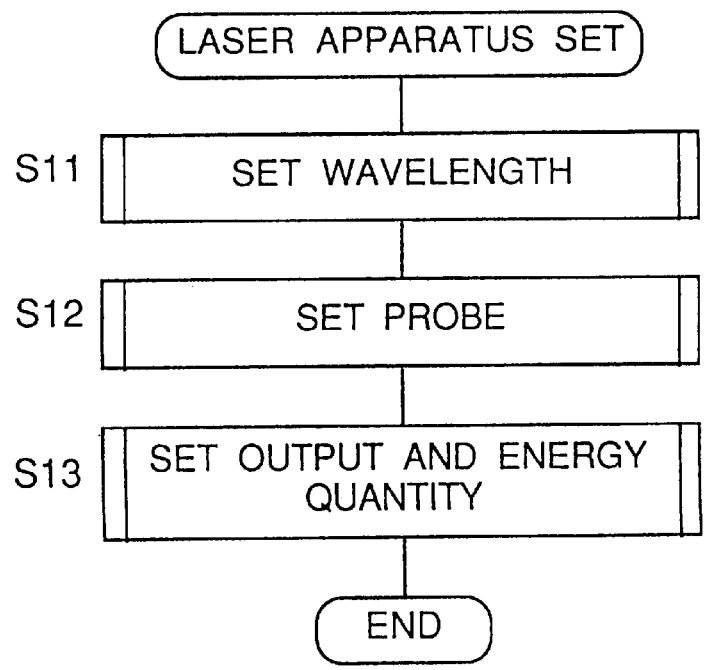

MEDICAL LASER APPARATUS AND DIAGNOSTIC/TREATMENT APPARATUS USING THE MEDICAL LASER APPARATUS

CROSS-REFERENCE TO RELATED APPLICATION

This is a divisional application of Ser. No. 08/545,101 filed Oct. 19, 1995 now U.S. Pat. No. 6,214,033, which is a continuation-in-part of Ser. No.08/174,370 filed Dec. 28, 1993, now abandoned.

BACKGROUND OF THE INVENTION

The present invention relates to a medical laser apparatus to be used as a light source for a diagnostic/treatment apparatus which treats a focus of a tumor such as a cancer or the like through irradiation of light to the focus. When light having a wavelength coinciding with the absorption wavelength of a photosensitizer which has an affinity to the focus and has been preliminarily accumulated in the focus is irradiated to the focus, the photosensitizer is excited, making it possible to diagnose or treat the focus. The present invention relates alike to a diagnostic/treatment apparatus using the medical laser apparatus.

In accordance with the development of electronic medical-care technology, photodynamic diagnosis (referred to as PDD hereinbelow) and the photodynamic therapy (referred to as PDT hereinafter), each utilizing laser light, have made rapid progress recently. In PDD and PDT, a photosensitizer having affinity to a tumor and capable of a photochemical reaction, e.g., an emission of fluorescence or a cellcidal action, is accumulated in a focus of the tumor beforehand, and then light is irradiated to the focus, which induces the excitation of the photosensitizer, to thereby permit diagnosis of the focus by measuring the emitted fluorescence (PDD) or treatment of the focus by the cellcidal action (PDT). It is preferable that the wavelength of the light irradiated to the focus coincides with the absorption wavelength of the photosensitizer in order to efficiently excite the photosensitizer, and therefore a laser light source has been generally employed as a light source of the light irradiating to the focus. In this case, the laser light source is fitted to the absorption wavelength of the photosensitizer being used.

A dye laser which uses hematoporphyrin as a photosensitizer and an excimer laser as a laser light source (referred to as an excimer dye laser hereinbelow) has been often used in the above-described type of diagnostic/treatment apparatus for diagnosing and treating cancers, as is discussed in Japanese Patent Publication Nos. 63-2633 (2633/1988) and 63-9464 (9464/1988). The conventional diagnostic/treatment apparatus using the laser device disclosed in the noted publications will be described with reference to FIG. 4.

FIG. 4 schematically shows the constitution of a cancer diagnostic/treatment apparatus using a conventional laser apparatus. In FIG. 4, A is a focus of a cancer and B indicates the peripheral part of the focus A where hematopor-phyrin has been absorbed as-a photosensitizer beforehand. A first pulse source 31 for diagnostic purposes and a second pulse source 32 for treatment purposes are both constituted of an excimer dye laser. An excimer dye laser for exciting the first and second dye lasers 31, 32 repeatedly oscillates with an oscillating wavelength 308 nm and pulse width 30 ns while varying the energy in the range of several mJ–100 mJ. The oscillating wavelength of the first pulse source 31 is 405 nm and that of the second pulse source 32 is 630 nm. The first and second pulse sources 31, 32 are switched by a switching part 33. The other reference numerals represent: 34 a light transmission line; 35 a TV camera; 36 a TV monitor; 37 a half mirror; 38 a spectroscope; 39 a spectrum analyzing part; and 40 a display unit.

The diagnosing/curing apparatus of the above-described constitution operates as follows.

When a cancer is to be diagnosed, a laser light of the wavelength 405 nm generated from the first pulse light source 31 is irradiated to the focus A and the peripheral part B through the switching part 33 and the light transmission line 34. A fluorescence image of the wavelength 630 nm, 690 nm excited by the laser light of 405 nm wavelength is photographed by the TV camera 35 and displayed for observation on the screen of the TV monitor 36. At the same time, the fluorescence image is extracted by the half mirror 37 and divided by the spectroscope 38. The spectrum is analyzed in the spectrum analyzing part 39 and the wavelength of the spectrum is displayed by the display unit 40. In order to treat the cancer, then, a laser light of the wavelength 630 nm produced by the second pulse light source 32 is, through the switching part 33 and the light transmission line 34, irradiated to the focus A. The operation mode is subsequently switched to the diagnosing mode again to thereby confirm the result of the treatment. The cancer is diagnosed and treated by repeatedly switching the modes as above.

In addition to the fact that the fluorescence peculiar to hematoporphyrin is efficiently excited by the light of the wavelength 405 nm, adverse influences resulting from scattering light can also be restricted due to the difference of the wavelengths 630 nm and 690 nm of the fluorescence, the first pulse light source 31 for diagnostic purposes thus uses the wavelength 405 nm. Meanwhile, the second pulse light source 32 for treatment purposes is set at the wavelength 630 nm because the laser light of the wavelength 630 nm transmits well through the tissue and is efficiently absorbed in hematoporphyrin.

In addition to the aforementioned example, the photosensitizers in (Table 1) below are proposed for use in PDD and PDT and also the lasers shown in (Table 1) are tried to be used as a laser light source for PDT.

TABLE 1

| Photo-sensi-tizer | Absorption wave-length [nm] | Laser light source (projection wavelength [nm]) | Disadvantages of laser devices |
|---|---|---|---|
| HpD | 630 | Excimer dye laser<br>Argon dye laser (624 ± 6.5 nm) | *Deterioration of solution of coloring matter is fast<br>*Bulky and expensive |
|  |  | Gold vapor laser (627.8 nm) | *Necessary to warm up for 30 min. or more<br>*Life of gas and oscillating tube is short<br>*Bulky and expensive. |
| PH-1126 | 650 | Krypton laser (647 nm) | *Life of gas is short<br>*Bulky and expensive |
| NPe6 | 664 | Argon dye laser (667 ± 5 nm) | *Deterioration of solution of coloring matter is fast<br>*Bulky and expensive |

A drawback of the conventional diagnostic/treatment apparatus of cancers resides in the fact that the wavelength of the projected laser light is difficult to control.

In other words, it is necessary to make the wavelength of the laser light coincides with the absorption band of the photosensitizer so as to efficiently excite the photosensitizer. Generally, it is not possible for the gas laser (Table 1) to meet the absorption band of a plurality of the photosensitizers. Moreover, it is difficult for the gas laser to have a wavelength which coincides with the maximum absorption wavelength of even a single photosensitizer. Although a dye laser as depicted with reference to the above conventional example has been employed to solve the problem, it is necessary to exchange the solution of a coloring matter in order to change the oscillating wavelength of the dye laser. Therefore, a plurality of dye lasers corresponding to a plurality of different kinds of solutions of a coloring matter should be prepared and exchanged for every wavelength if the wavelength of the laser light is required to be changed, for instance, when the photosensitizer being used is changed or when the wavelength of the laser light is changed during treatment relative to that used during diagnoses.

In the case where the dye laser is used, therefore, the diagnostic/treatment apparatus becomes disadvantageously bulky in size to accommodate a plurality of different kinds of coloring matter solutions and a switching of the solutions.

A second disadvantage of the diagnostic/treatment apparatus using the dye laser is that the solution of a coloring matter of the dye laser easily deteriorates, inviting a change of the wavelength of the resultant laser light or a decrease of the output. Since the safety of the laser light is an essential and indispensable condition to ensure the effect of PDD and especially PDT, a substantial problem of the dye laser arises when the solution of the coloring matter should be exchanged or a circulator of the coloring matter should be cleaned frequently. Further, the wavelength of the laser light is undesirably changed or the laser output is decreased during the irradiation if the solution used in the dye laser easily degrades, that is, the irradiating condition of the laser light should be set with such changes in the wavelength or output as above taken into consideration and, the change of the laser light should be arranged to be detected.

Thirdly, when the wavelength is converted by the dye laser, the full width at half maximum (FWHM) of the wavelength of the obtained laser light expands to at least 10 nm or so. If the full width at half maximum is wide, the laser light increasingly shifts from the absorption band of the photosensitizer, thus worsening the exciting efficiency of the photosensitizer. Although it may be arranged to reduce the full width at half maximum of the dye laser by using a band pass filter or a diffraction grating, only the excessive component is cut, but the exciting efficiency is left unimproved.

A fourth drawback is the poor converting efficiency of energy of the dye laser when the wavelength is converted. Therefore, the excimer laser, etc. used as a light source to excite the dye laser is required to generate a high output in order to achieve sufficient energy from the converted laser light. In other words, the conventional medical laser apparatus and the diagnostic/treatment apparatus of cancers using the conventional medical laser apparatus are liable to be bulky and expensive.

A fifth drawback inherent in the prior art resides in the need for two light sources for diagnostic purposes and for treatment purpose as well as the switching mechanism to switch the light sources. The apparatus consequently is bulky and expensive and moreover, it is inconvenient to switch the light sources and erroneous manipulation can occur.

SUMMARY OF THE INVENTION

The object of the present invention is therefore to provide, with eliminating the aforementioned drawbacks of the conventional apparatuses, a compact and inexpensive medical laser apparatus which achieves laser light of the oscillating wavelength fit for a plurality of kinds of photosensitizers and also a plurality of exciting conditions thereof, and is maintenance-easy with a narrow full width at half maximum and good exciting efficiency.

A further object of the present invention is to provide a diagnostic/treatment apparatus using the medical laser apparatus which realizes both diagnosis and treatment by a single light source to thereby make a diagnosis simultaneously during the treatment.

In accomplishing these and other objects, according to a first aspect of the present invention, there is provided a medical laser apparatus designed to diagnose or treat a focus by irradiating light from a light source to the focus where a photosensitizer having an affinity to the focus has been preliminarily accumulated to thereby excite the photosensitizer, the apparatus- comprising: a laser as the light source which is capable of controlling oscillating wavelength and which has a full width at half maximum which is narrower than a width of a band, where an energy absorption of the photosensitizer is equal to or more than 90% of the maximal value in the vicinity of the oscillating wavelength; and a wavelength controlling means for controlling the laser.

According to a second aspect of the present invention, there is provided a diagnostic/treatment apparatus designed to diagnose or cure a focus by irradiating light from a light source to the focus where a photosensitizer having an affinity to the focus has been preliminarily accumulated to thereby excite the photosensitizer, the diagnostic/treatment apparatus comprising: a medical laser apparatus which comprises a laser as the light source which is capable of controlling oscillating wavelength and which has a full width at half maximum which is narrower than a width of a band, where an energy absorption of the photosensitizer is equal to or more than 90% of the maximal value in the vicinity of the oscillating wavelength, and a wavelength controlling means for controlling-the laser; a light transmission line for guiding the laser light projected from the medical laser apparatus to the vicinity of the focus; an image transmission line for guiding fluorescence emitted from the photosensitizer excited by the laser light to observe the focus and a periphery thereof; a fluorescence separating means for separating only the fluorescence; and an image-picking-up/analyzing means for picking up and analyzing an image of the fluorescence obtained by the fluorescence separating means.

BRIEF DESCRIPTION OF THE DRAWINGS

These and other objects and features of the present invention will become clear from the following description taken in conjunction with the preferred embodiments thereof with reference to the accompanying drawings, in which:

FIG. 9 is a flowchart showing a diagnosing step of FIG. 8;

FIG. 10 is a f flowchart showing a laser apparatus setting step of FIG. 8;

DETAILED DESCRIPTION OF THE PREFERRED EMBODIMENTS

Figure 1:
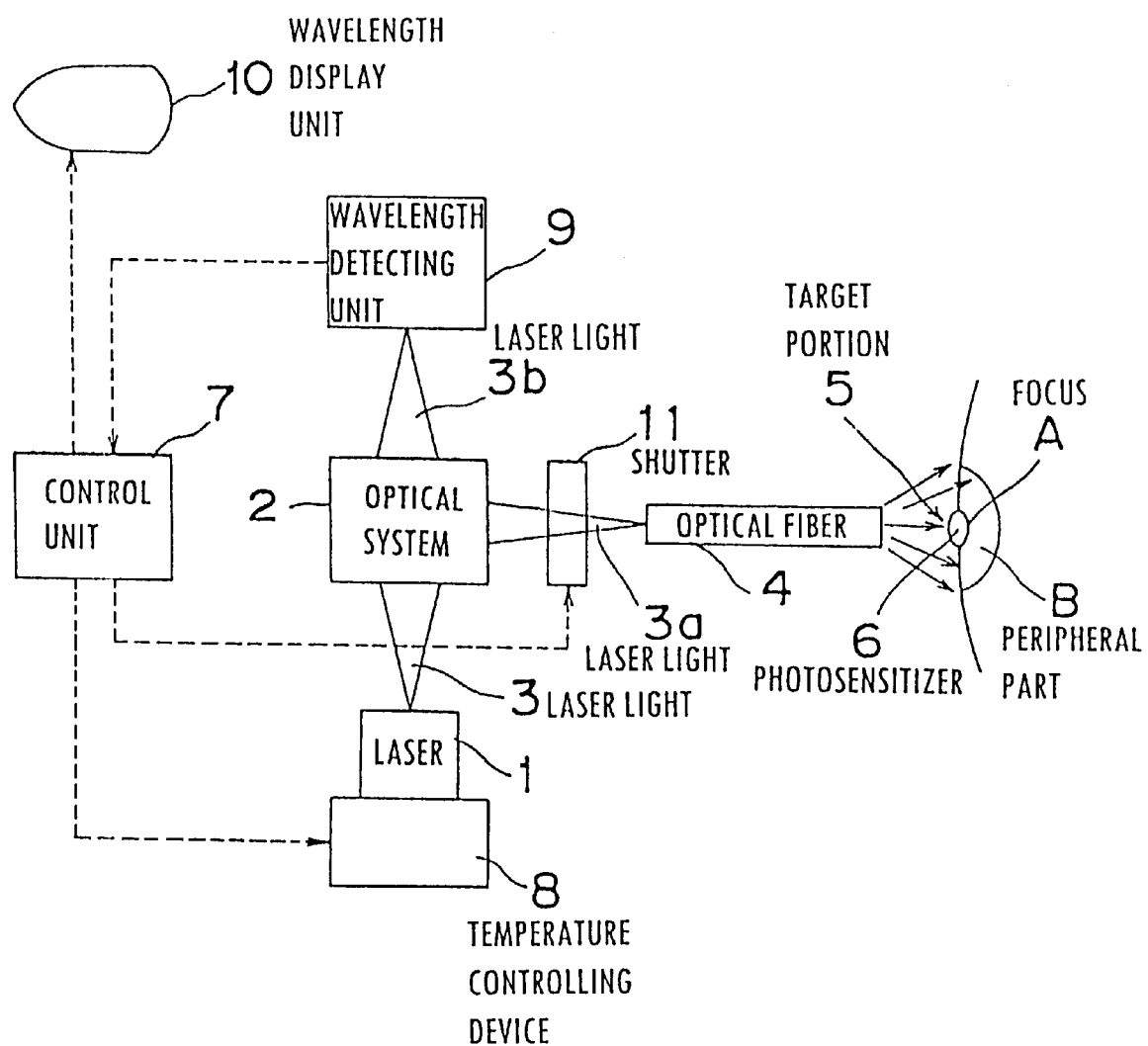
FIG. 1 is a block diagram showing the constitution of a medical laser apparatus according to a first embodiment of the present invention.

Before the description of the present invention proceeds, it is to be noted that like parts are designated by like reference numerals throughout the accompanying drawings.

First Embodiment

A medical laser apparatus according to a first embodiment of the present invention will be discussed hereinbelow with reference to the accompanying drawings.

The constitution of a medical laser apparatus according to a first embodiment of the present invention is shown in FIG. 1. Referring to FIG. 1, an AlGaInP semiconductor laser 1 has an oscillating frequency 664 nm, full width at half maximum (FWHM) of ±1 nm, temperature characteristic of the oscillating wavelength 0.2 nm/deg, and operable temperature range −100 through +80° C. during driving at 0° C. An optical system 2 separates a laser light 3 projected from the semiconductor laser 1 to an irradiating laser light 3a and a wavelength detecting laser light 3b. A photosensitizer 6 is preliminarily administered in a target portion to be treated including a focus A and a peripheral part B of the focus A. The other reference numerals indicate: 4 an optical fiber; 7 a control unit; 8 a temperature controlling device; 9 a wavelength detecting unit for detecting the wavelength of the laser light 3b; 10 a wavelength displaying unit; and 11 a shutter working as an automatic irradiation stopping unit in association-with the control unit 7.

The operation of the medical laser apparatus having the constitution as above will be described below.

The wavelength of the laser light 3 projected from the semiconductor laser 1 is determined by the temperature of the semiconductor laser 1. That is, when the temperature of the semiconductor laser 1 is varied in the range of −100 through +80° C. by the temperature controlling device 8, the wavelength of the laser light 3 is changed within 644 through 680 nm. Accordingly, the wavelength of the laser light 3 is obtained which is suited to the absorption wavelength of the using photosensitizer 6 and the purpose of the treatment.

In the instant embodiment, NPe6 (trade name of Nippon Petrochemical Co., Ltd.) of a chlorin group in (Table 1) is used as the photosensitizer 6. The temperature of the semiconductor laser 1 is set at 0° C. when the laser light 3 of the center wavelength 664 nm in the absorption band of 660 nm through 668 nm of the photosensitizer 6 is desired. On the other hand, the temperature of the semiconductor laser 1 is controlled to be −15° C. in order to obtain the laser light of the shorter wavelength 660 nm in the absorption band for a purposed to be described later. When the laser light 3 of the center wavelength 650 nm and the shorter wavelength 644 nm in the absorption band of 647 nm through 653 nm is to be-obtained with the use of PH-1126 (trade name of Hamari Chemicals, Ltd.) of a pheophorbide group (Table 1), the semiconductor laser is controlled to be −70° C. and −100° C., respectively. The full width at half maximum is narrower than a width of the absorption band, where an energy absorption of the photosensitizer is equal to or more than 90% of the maximal value in the vicinity of the oscillating wavelength.

Since the full width at half maximum is ±1 nm, the wavelength of the laser light 3 projected from the semiconductor laser 1 controlled at the temperature 0° C., 15° C., −70° C., and −100° C. is 663–665 nm, 659–661 nm, 649–651 nm, and 643–645 nm, that is, the energy of the laser light 3 is held within the absorption band of the photosensitizer 6 being used.

A part of the -laser light 3 from the controlled semiconductor laser 1 is separated by the optical system 2 and guided to the wavelength detecting unit 9 as the wavelength detecting laser light 3b. The detecting unit 9 detects the wavelength of the laser light 3b. The detected result is sent to the control unit 7. It is decided by the control unit 7 whether the laser light 3b matches a predetermined condition to control the wavelength thereof. The detecting result and the value of the wavelength is displayed by the wavelength displaying unit 10. The control unit 7 activates the automatic irradiation stopping unit 11 in case the laser light 3b does not match the predetermined controlling condition so as to shut the irradiating laser light 3a.

When the laser light 3 conforms to the predetermined controlling condition, the shutter 11 is opened and the irradiating laser light 3a is condensed into the optical fiber 4 to be irradiated to the target portion 5 from an end of the optical fiber 4.

As described hereinabove, the oscillating wavelength of the laser is controlled to thereby obtain the laser light of the wavelength of the narrow full width at half maximum which is suited to the absorption wavelength of a plurality of kinds of photosensitizers and the purpose of the treatment, so that the photosensitizers can be excited efficiently. Moreover, the laser apparatus is almost maintenance-free, compact in size and inexpensive.

Second Embodiment

A diagnostic/treatment apparatus of cancers according to a second embodiment of the present invention will be discussed with reference to FIGS. 2 and 3.

Figure 2:
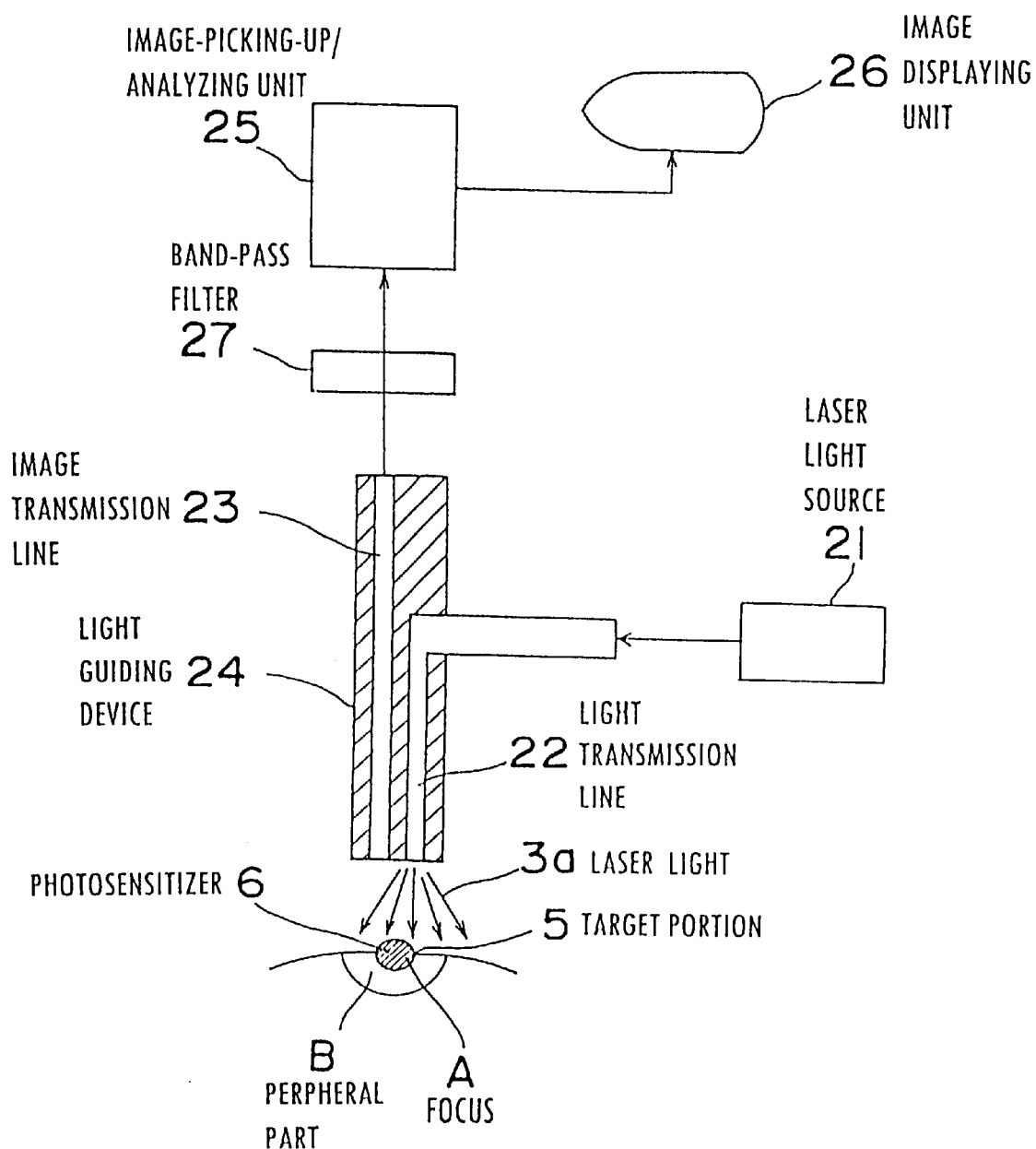
FIG. 2 is a block diagram showing the constitution of a diagnostic/treatment apparatus according to a second embodiment of the present invention.
Figure 3:
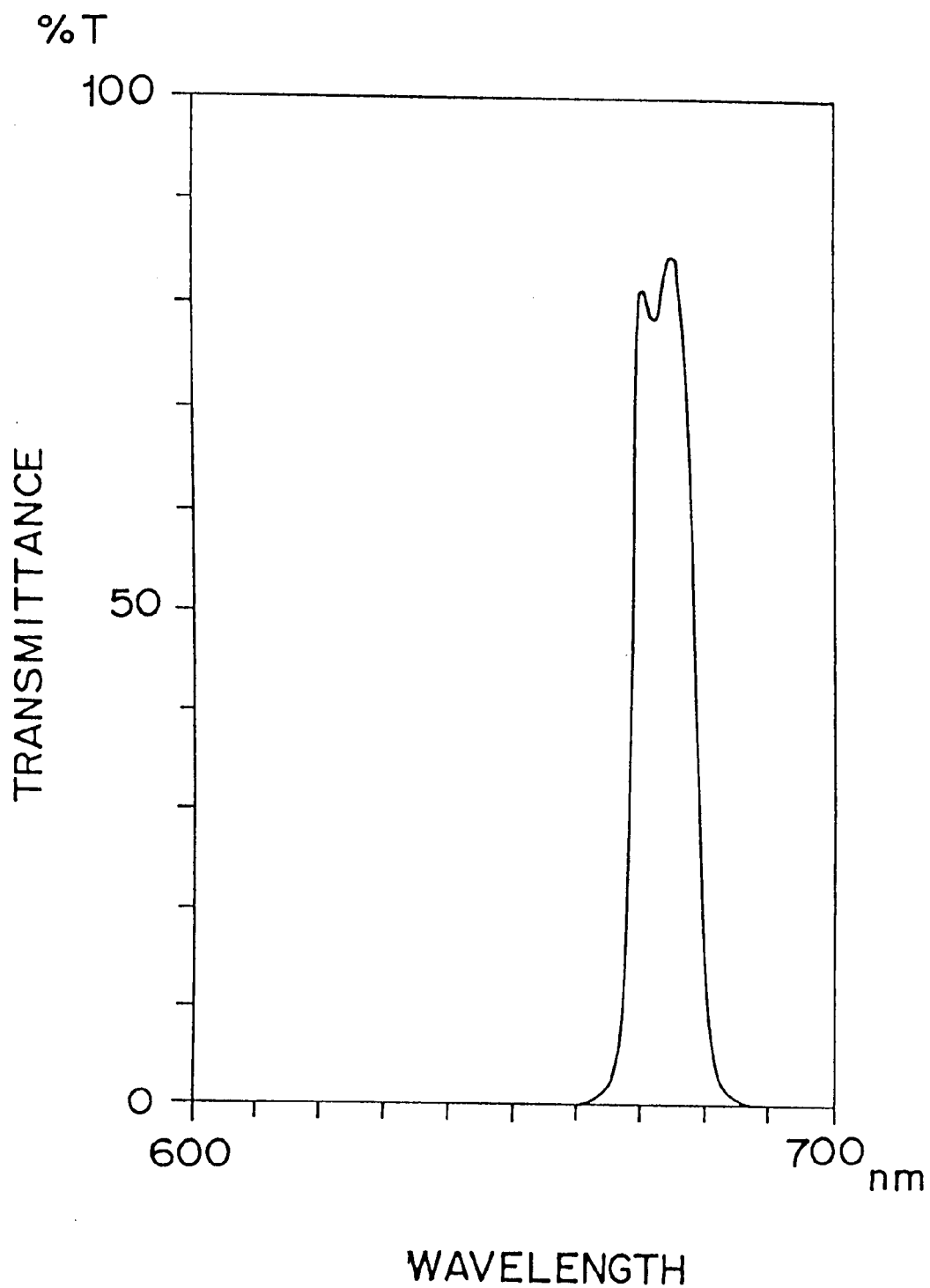
FIG. 3 is a characteristic diagram of a band pass filter used in the second embodiment of the present invention.
Figure 4:
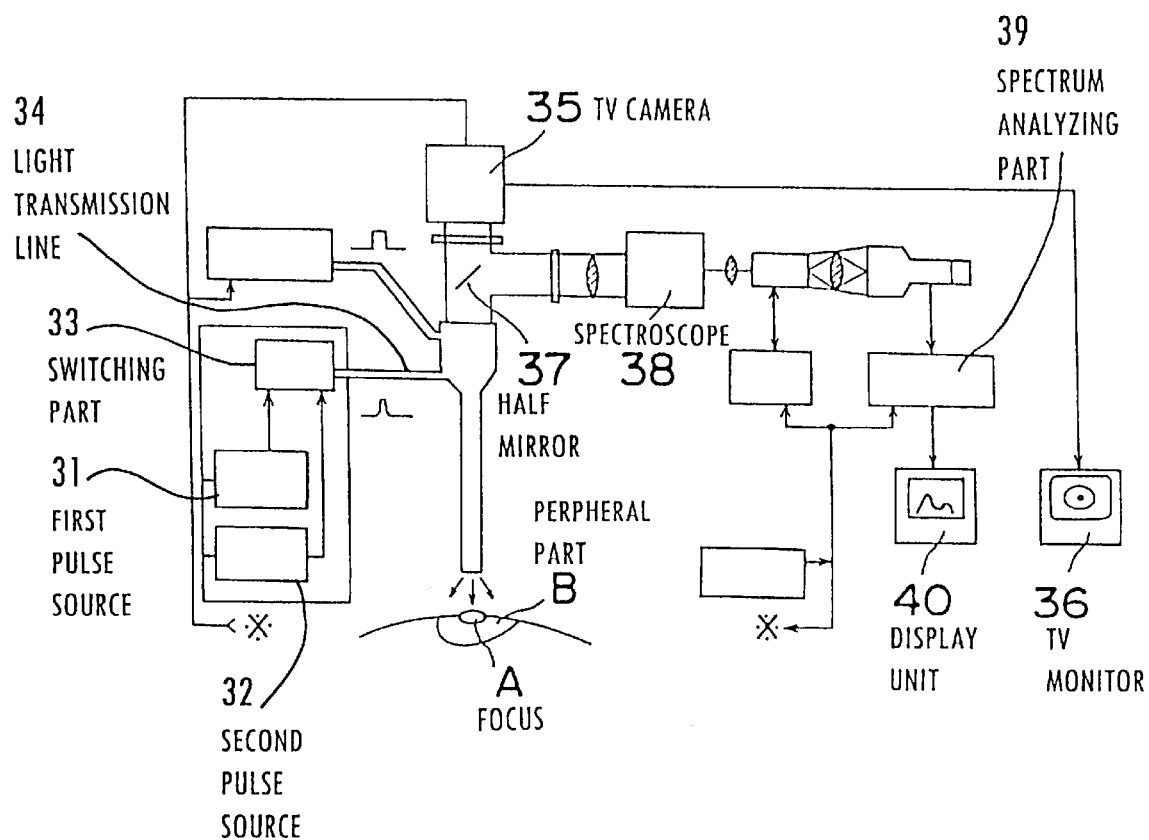
FIG. 4 is a block diagram showing the constitution of a diagnostic/treatment apparatus of cancers using a conventional laser apparatus.

FIG. 2 is a block diagram showing the constitution of the diagnostic/treatment apparatus of cancers according to the second embodiment of the present invention. In FIG. 2, reference numeral 21 denotes a laser light source which is the medical laser apparatus using the semiconductor laser disclosed in the foregoing first embodiment, 22 denotes a light transmission line through which the irradiating laser light 3a from the laser light source 21 is introduced to the vicinity of the focus, and 23 denotes an image transmission line through which an image of fluorescence is transmitted to observe the focus and the periphery of the focus. A light guiding device 24 incorporating the light transmission line 22 and the image transmission line 23 guides both the lines 22 and 23 to the vicinity of the focus. An image-picking-up/analyzing unit 25 picks up images in the vicinity of the focus through the image transmission line 23 and analyzes the images. The analyzing result is displayed by an image displaying unit 26. A band-pass filter 27 with a considerably narrow band width, i.e., approximately ±3 nm to the designated wavelength is composed of a dielectric multi-layer film (for example, a total dielectric interference filter DIF of Vacuum optics Corporation of Japan having the characteristic shown in FIG. 3). The band-pass filter 27 allows only the light of the wavelength in the vicinity of that of fluorescence of the photosensitizer being used separately from the irradiating laser light 3a to pass. The passing wavelength is approximately 670 nm when the photosensitizer of a chlorin group is used, or approximately 654 nm when the photosensitizer of a pheophorbide group is used. The band-pass filter 27 is placed on an optical axis connecting the image transmission line 23 with the image-picking-up/analyzing unit 25. It is to be noted here that the band-pass filter 27 can be equipped with a plurality of band-pass filters respectively corresponding to a plurality of photosensitizers, and also a switching means (not shown) to switch the band-pass filters. The remaining reference numerals, for instance, 5 and the like represent the same parts as in FIG. 1.

The operation of the diagnostic/treatment apparatus of cancers constituted in the above-described arrangement will be depicted below.

In the first place, the irradiating laser light 3a projected from the laser light source 21 is irradiated via the light transmission line 22 to the target portion 5 where the photosensitizer has been preliminarily accumulated. At this time, the laser light 3a is controlled by the temperature controlling device to attain the center wavelength of the absorption band of the photosensitizer so that the treatment results in the optimum effect. In other words, the wavelength of the laser light 3a is controlled to be 664 nm and 650 nm when and PH-1126 are used as the photosensitizer, respectively. The controlling operation has been described earlier in the first embodiment.

When the laser light 3a is irradiated to the target portion 5, the focus A is selectively treated by the action of the photosensitizer accumulated there beforehand. At the same time, the photosensitizer in the focus A is excited by the laser light 3a and consequently emits fluorescence of the specified wavelength as described before. The target portion is thus diagnosed by analyzing the image of fluorescence. The fluorescence shows the wavelength considerably approximate to that of the irradiating laser light 3a and has the weak intensity, and therefore is strongly influenced by the scattering light of the laser light 3a. It is hence conventionally generally difficult to pick up and analyze the image of fluorescence.

As such, the fluorescence is guided through the band-pass filter 27 via the image transmission line 23 according to the instant embodiment. More specifically, the fluorescence is passed through the band-pass filter 27 which has such characteristic as exemplified in FIG. 3 and allows only the fluorescence emitted from the photosensitizer being used to pass while shutting the irradiating laser light 3a, whereby the influences of the scattering light of the laser light 3a are eliminated. As a result, the image of fluorescence alone is inputted to the image-picking-up/analyzing unit 25. The image-picking-up/analyzing unit 25 picks up and analyzes the image data of fluorescence, the result of which is displayed at the image displaying unit 26 such as a television and recorded in a recording unit such as a VTR. By observing the display, the focus A can be diagnosed in real time even in the middle of the treatment.

It is also possible to control and shift the wavelength of the irradiating laser light 3a from that of the fluorescence with an aim to improve the separation of the fluorescence (S) from the scattering light (N) of the irradiating 14 laser light 3a (S/N ratio). That is, the irradiating laser light 3a may be controlled to be shifted from the center wavelength in the absorption band of the photosensitizer being used (e.g., 664 nm or 650 nm when NPe6 or PH-1126 is used) to be away from the wavelength of the fluorescence within the absorption band (e.g., 660 nm or 644 nm when NPe6 or PH-1126 is used). If the wavelength of the irradiating laser light 3a is controlled as above, the S/N ratio is improved. At the same time, since the energy of the irradiating laser light 3a is kept within the absorption band of the photosensitizer as described earlier in the first embodiment, the treatment effect is hardly deteriorated.

The oscillating, wavelength of the laser light 3 can be made variable also in a diagnostic/treatment apparatus which uses only a specific photosensitizer (for instance, NPe6 or PH-1126) within the range of the effective absorption band of the photosensitizer (e.g., 664±5 nm or 650±10 nm in the case of NPe3 or PH-1126).

Since the wavelength of the irradiating laser light 3a can be controlled easily in the medical laser apparatus of the embodiments of the present invention, even when the concurrent diagnosis with the treatment becomes unnecessary, it is possible to return the wavelength of the irradiating laser light 3a to the center wavelength of the absorption band of the photosensitizer, that is, the optimum wavelength for the treatment. Moreover, it is an advantage of the medical laser apparatus of the embodiments to display whether the wavelength of the laser light 3 conforms to the controlling condition. If the wavelength of the laser light 3 is not in compliance with the controlling condition, the laser light is shut off as mentioned before.

Accordingly, due to the band-pass filter provided in the diagnostic/treatment apparatus of the embodiments, it becomes possible to execute diagnosis and treatment concurrently using a single laser light source. The wavelength of the laser light is controlled by the wavelength controlling unit to be away from the wavelength of the fluorescence emitted by the photosensitizer within the absorption band of the photosensitizer, so that the S/N ratio ensuring stable images during the concurrent diagnosis with the treatment is satisfied.

Although the laser in the first embodiment is a semiconductor laser, the other kinds of lasers can be employed so long as the full width at half maximum is narrow and the oscillating wavelength of the laser light is variable. Needless to say, the semiconductor laser 1 is not limited to the one having the characteristic described in the first embodiment. For example, the laser can be made up of an external resonating type semiconductor laser which wavelength is controlled by change of resonance from its external.

Further, although the temperature is controlled in the arrangement of feedback control by means of the wavelength detecting unit 9 in the first embodiment, it is possible to control the wavelength correctly if a memory means storing the relationship between the temperature and the oscillating wavelength of the using semiconductor laser is provided to control the temperature of the semiconductor laser based on the relationship.

As is fully described hereinabove, the medical laser apparatus is provided with the laser as a light source and the wavelength controlling unit for the laser. This laser emits the laser light of the narrow full width at half maximum and the oscillating wavelength of the laser light is variable. Therefore, the medical laser apparatus is able to achieve the oscillating wavelength suitable for the kind of the photosensitizer being used as well as the exciting condition of the photosensitizer, and thus efficiently excite the photosensitizer. Moreover, the medical laser apparatus is advantageously almost maintenance-free, compact and inexpensive.

According to the diagnostic/treatment apparatus of the present invention, since the image of fluorescence is displayed by the image displaying unit also during the treatment of the focus, it becomes possible to diagnose and treat the focus using a single light source, and to make diagnosis of the focus during the treatment in the simple and compact structure. The diagnostic/treatment apparatus is easy to handle.

A third embodiment of the present invention will be discussed below.

The third embodiment is effective in solving the following inconveniences. When neither permeability of irradiating light to a focus when the irradiating light reaches the focus nor irradiation energy of irradiating light relevant to a treatment effect through excitation efficiency characteristics of a photosensitizer is controlled, and when a wavelength of a laser light shifts from an optimum absorption wavelength of the photosensitizer, there is a disadvantage that photochemical reaction quantity of the irradiating light having an equal output intensity is reduced due to the degradation of an excitation effect of the photosensitizer. Furthermore, when a specifically set output cannot be obtained due to an abnormality of laser, a protection means built in the laser apparatus operates to cause a disadvantage that the treatment cannot be effected. There is a further disadvantage that irradiating light having an equal output cannot be obtained with respect to an emission laser light having an equal output (in output intensity and intensity distribution) due to the type of a laser probe to be used in connection with a main unit of the diagnostic/treatment apparatus, a variation and deterioration with an elapse of time of transfer characteristics of each probe and so forth.

In order to solve the above-mentioned disadvantages, the diagnostic/treatment apparatus of the third embodiment comprises: irradiation energy quantity control means for controlling the irradiation energy quantity of irradiating light; control means for controlling the laser so that the irradiation energy quantity of the irradiating light becomes a specified quantity; irradiating light characteristic measuring means for measuring irradiation characteristics of the irradiating light irradiated from an optical transmission path for transmitting light from a light source to a focus; a plurality of laser units which serve as the light source; oscillation control means for controlling the total oscillation characteristics by individually controlling the plurality of laser units; and wavelength correction means for correcting a control target value of the irradiation energy quantity by the wavelength of the irradiating light.

Figure 5:
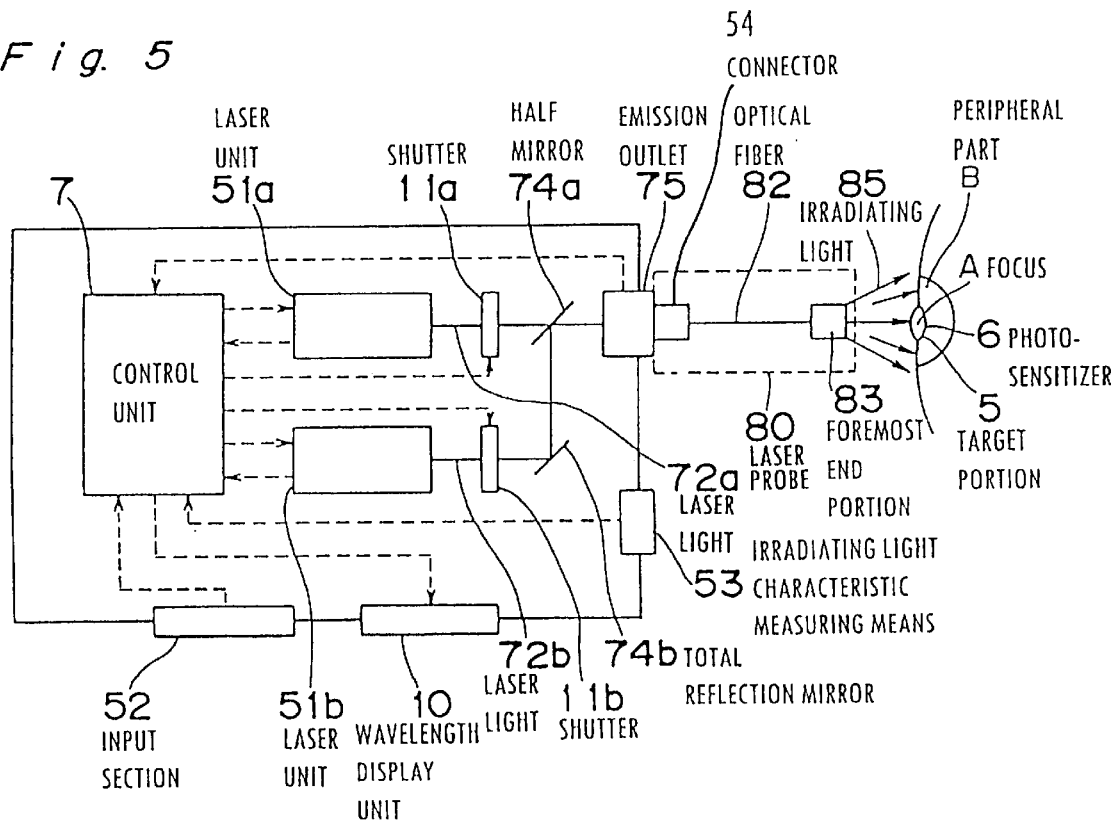
FIG. 5 is a block diagram of a apparatus according to a third diagnostic/treatment apparatus according to a third embodiment of the present invention.
Figure 6:
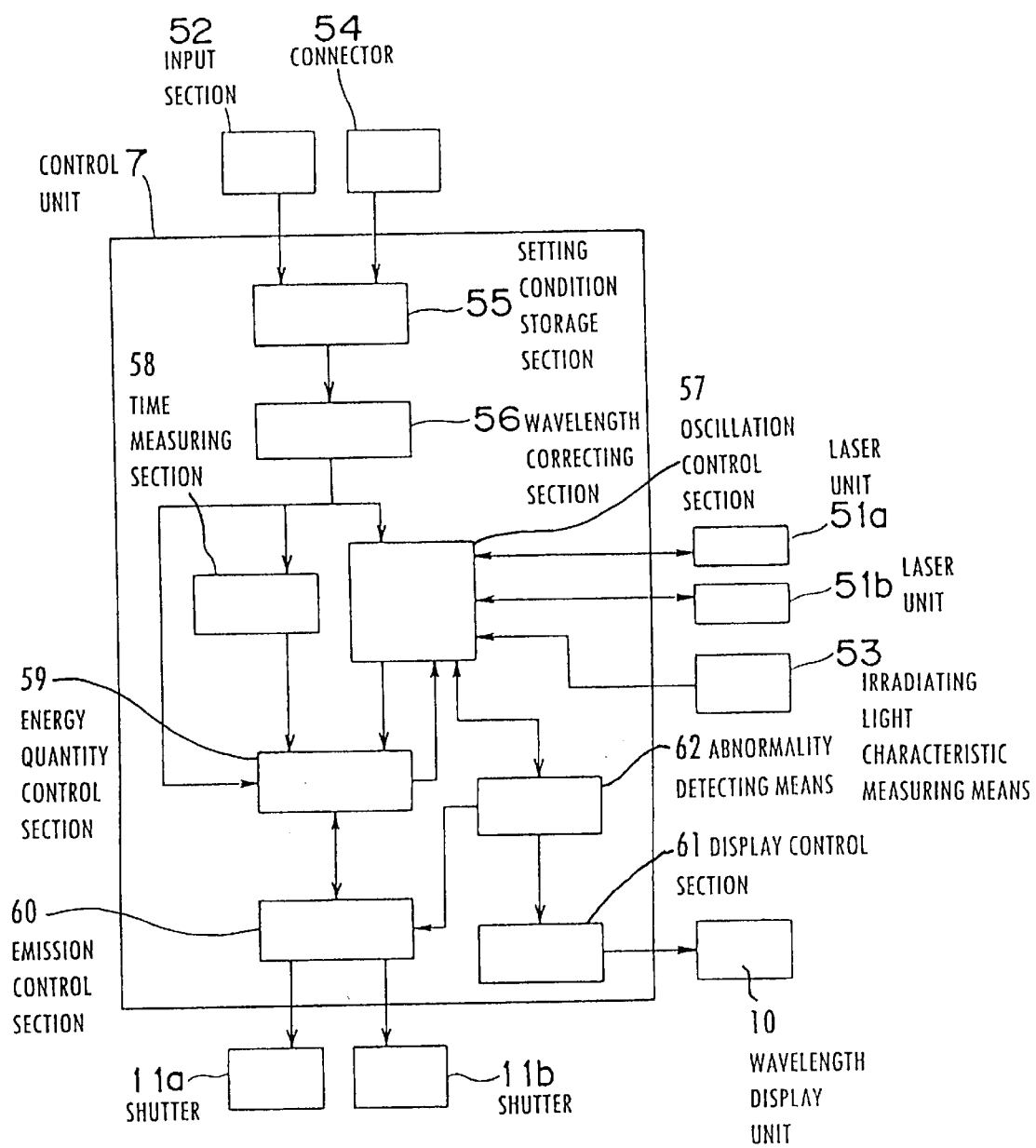
FIG. 6 is a detailed block diagram of control means of the diagnostic/treatment apparatus of the third embodiment of the present invention.

Practically, as shown in FIG. 5, there are provided two semiconductor laser units 51a and 51b each of which is provided with a semiconductor laser 1 shown in FIG. 1, the temperature controlling device 8 for controlling the wavelength of emission light by controlling the temperature of the semiconductor laser 1, and a wavelength detecting unit 9 for detecting the output characteristics of wavelength, output intensity, oscillation efficiency and so forth of the emission light. Emission beams of laser light 72a and 72b emitted respectively from the units 51a and 51b, are guided to an emission outlet 75 via shutters 11a and 11b, a half mirror 74a, and a total reflection mirror 74b. There is provided the control unit 7, and as 'shown in FIG. 6, it is comprised of: a setting condition storage section 85; a wavelength correcting section 56; an oscillation control section 57; a time measuring section 58; an energy quantity control section 59; an emission control section 60; a display control section 61; and an abnormality detecting means 62. The oscillation control section 57 has a function of individually controlling the semiconductor laser units 51a and 51b, and is comprised of an oscillation and stop control section, a wavelength control section, an output section, and an irradiating light intensity control section, and an irradiating light converting section (all of these sections are not shown). It is to be noted that neither description nor illustration is provided for normal functional sections of control means, a CPU and so forth owned by an ordinary diagnostic/treatment apparatus. There are further shown an input section 52 for inputting a variety of operation conditions, the wavelength displaying unit 10, and an irradiating light characteristic measuring means 53 which is comprised of an irradiation outlet for connecting a foremost end portion 83 of the laser probe 80 and a measuring section (these sections are not shown). The laser probe 80 is comprised of a connector 54 to be connected to the emission outlet 75, an optical fiber 82, and the foremost end portion 83. A part A is a focus, and a photosensitizer 6 is preliminarily administered in a portion to be treated 5 including the focus A and a peripheral portion B of the focus A. A reference numeral 85 denotes irradiating light to be irradiated from the foremost end portion 83 to the portion to be treated 5.

Figure 8:
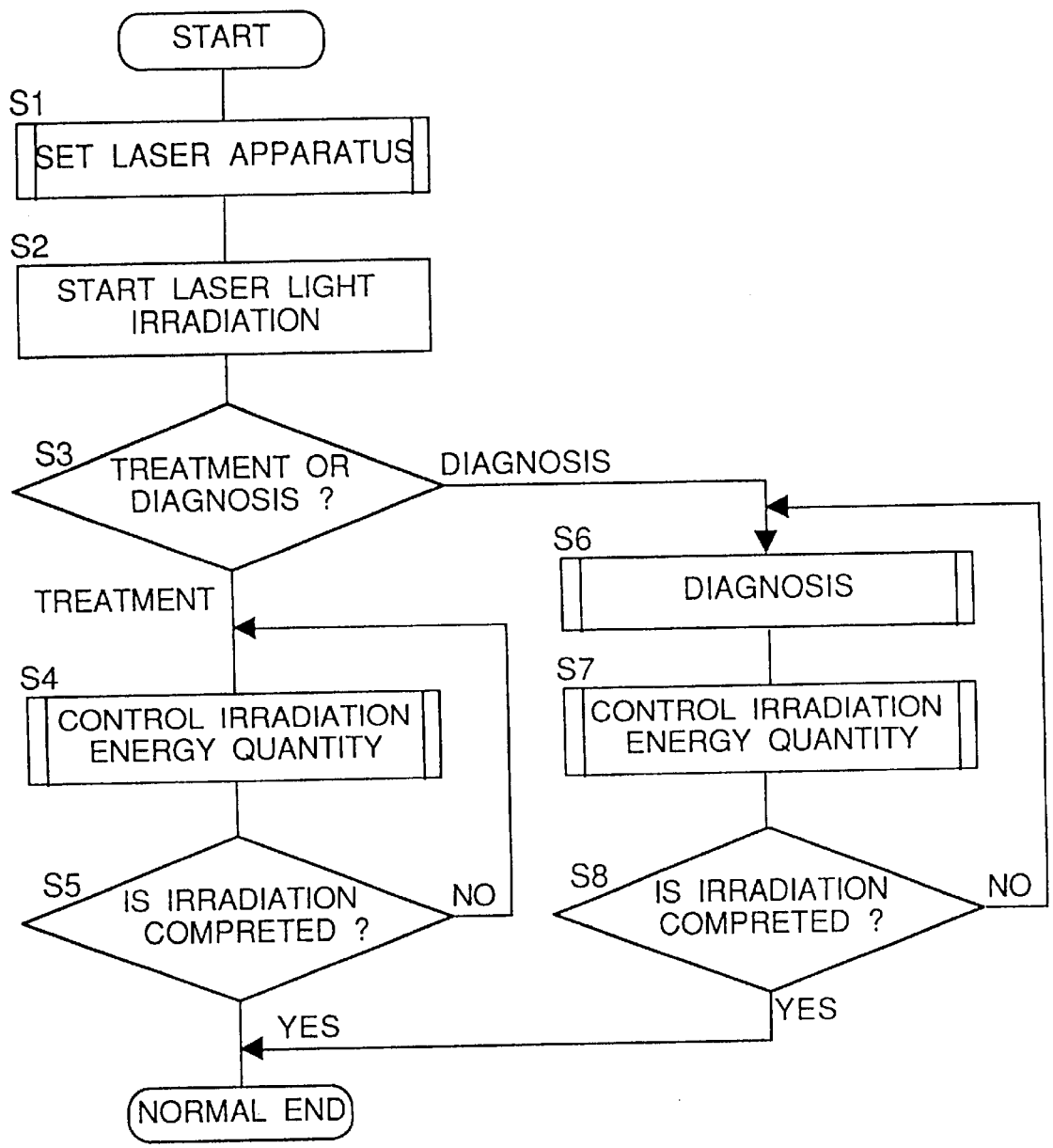
FIG. 8 is a schematic flowchart showing a procedure of treatment and/or diagnosis by means of the diagnostic/treatment apparatus of the third embodiment of the present invention.

FIG. 8 is a schematic flowchart showing a procedure of treatment and/or diagnosis by means of the diagnostic/treatment apparatus of the third embodiment of the present invention.

Setting of the laser apparatus is performed in step S1, laser light irradiation is started in step S2, and selection between treatment and diagnosis is performed in step S3. When treatment is selected in step S3, the program flow proceeds to step S4 to control an irradiation energy quantity in step S4. Then, it is decided whether or not the irradiation is completed in step S5. When the irradiation is not completed, the operations of step S4 and step S5 are repeated when the irradiation is completed in step S5, the program flow terminates as the result of correct achievement of the treatment (which is indicated in FIG. 8 as "normal end"). Otherwise, when diagnosis is selected in step S3, the program flow proceeds to step S6 to perform diagnosis and then proceeds to step S7 to control an irradiation energy quantity in step S7, and it is decided whether or not the irradiation is completed in step S8. When the irradiation is not completed, the operations of step S6 through step S8 are repeated. When the irradiation is completed in step S8, the program flow terminates as the result of the correct achievement of the treatment.

FIG. 9 is a flowchart showing the diagnosing operation in step S6 of FIG. 8. According to this flowchart, an image of fluorescence is extracted by a bandpass filter (fluorescence light separating means) 27 in step S61. Then, the image of fluorescence is analyzed in step S62. Then, the analyzed image of fluorescence is displayed in the displaying unit 10 in step S63.

FIG. 10 is a flowchart showing the laser apparatus setting operation in step S1 of FIG. 8. According to this flowchart, setting of wavelength is performed in step S11, setting of the probe is performed in step S12, and setting of output and energy quantity is performed in step S13.

Figure 11:
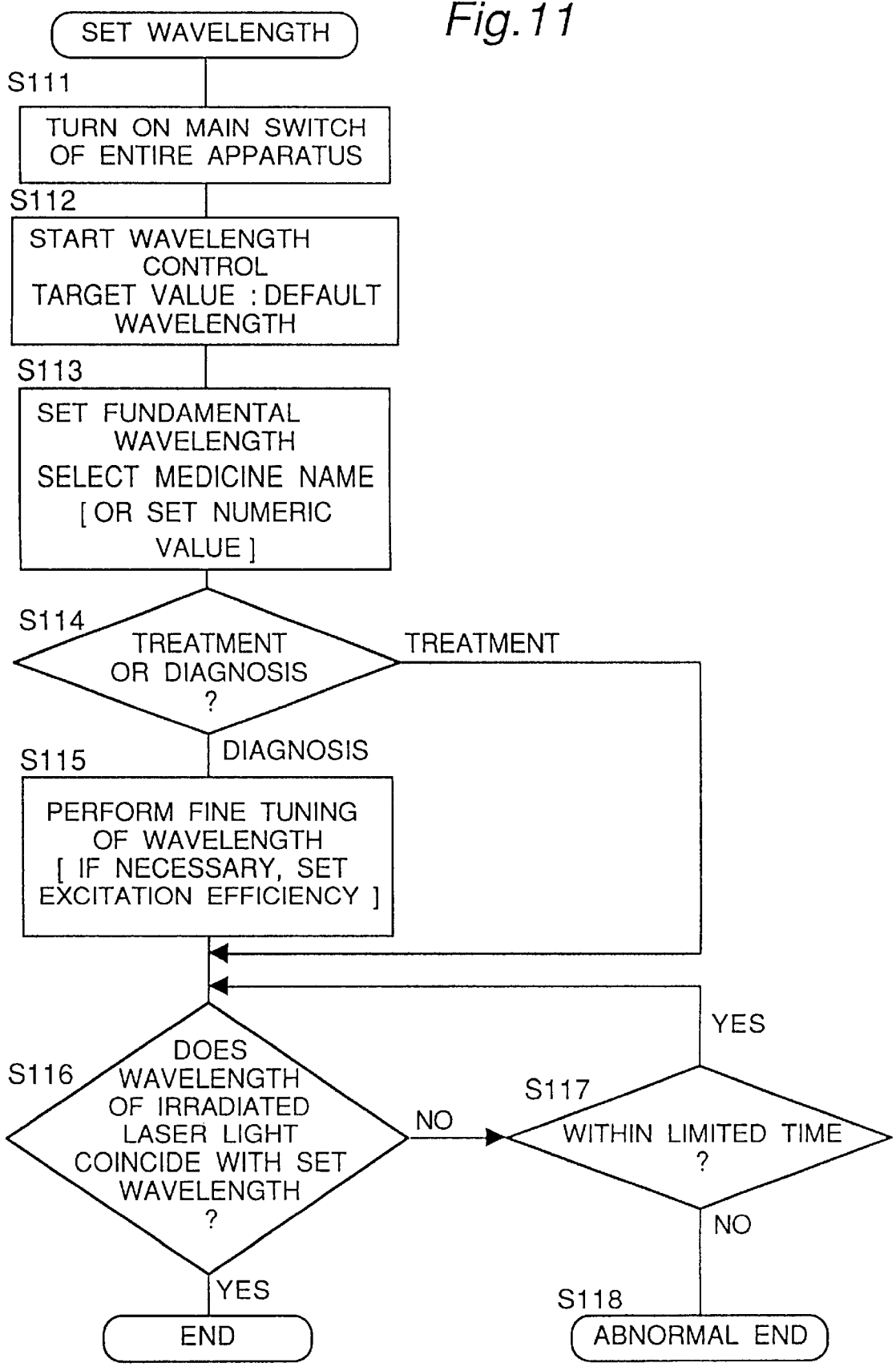
FIG. 11 is a flowchart showing a wavelength setting step of the FIG. 10.

FIG. 11 is a flowchart showing the wavelength setting operation in step S1 of the FIG. 10. According to this flowchart, a main switch of the entire apparatus is turned on in step S111, and wavelength control is started in step S112. In this case, the laser wavelength is set to a default wavelength which is a target value. In the present embodiment, the wavelength of the laser light of the semiconductor laser is controlled by temperature. For example, in the present embodiment, the semiconductor laser is cooled down to a temperature of 0° C. in order to obtain a wavelength of 664 nm in conformity to an absorption wavelength characteristic of a photosensitizer NPe6 to be used as one example. The "wavelength control start" as described above means start of a temperature control targeted at the temperature of 0° C. In this case, the default wavelength is 664 nm. The default wavelength may be fixed in the shipping stage of the apparatus, or the previously used condition-may be used as the default value.

The above-mentioned operation is an operation concerning temperature control of the semiconductor laser, and therefore the operation is achieved by controlling the temperature controlling device 8 included in each of laser units 51a and 51b by the oscillation control section 57 based on the default wavelength stored in the setting condition storage section 55.

Subsequently, setting of a fundamental wavelength is performed in step S113. In this case, selection of a medicine name or numerical value setting is performed. The fundamental wavelength is the optimum absorption wavelength of a. photosensitizer to be used for treatment, and the fundamental wavelength of, for example,of the present embodiment is 664 nm. The wavelength depends on the photosensitizer to be used, and therefore, when the photosensitizer is changed, the wavelength of the laser light is required to be changed according to the photosensitizer. That is, when the photosensitizer is decided, the fundamental wavelength thereof is decided. Therefore, in setting the wavelength of the apparatus, the wavelength can be selected by the name of the
photosensitizer to be used other than direct input of the intended wavelength. For example, names of plural photosensitizers may be displayed in the displaying unit 10 of the apparatus. Whenis selected from names at the input section 52, the fundamental wavelength is set to 664 nm. When PH-1126 is selected, the wavelength is set to 650 nm. Further, the fundamental wavelength can be directly set (numerically set) at the input section 52 so that even a photosensitizer of which name is not listed in the names of the photosensitizers preparatorily stored in the apparatus, such as a photosensitizer newly developed can be used.

Subsequently, in step S114, selection between treatment and diagnosis is performed. When-diagnosis is selected, the program flow proceeds to step S115. When treatment is selected, the program flow proceeds to step S116. In step S115, fine tuning of the wavelength is performed. If required, excitation efficiency is set. When diagnosis is performed concurrently with treatment as described in the second embodiment, an image of fluorescence is obtained from an observed image by the band-pass filter (fluorescence light separating means) 27 which interrupts the irradiating laser light and transmits is only fluorescence light. In the above stage, in order to improve a signal-to-noise ratio SIN of the fluorescence light to be transmitted (S) to the irradiating laser light to be cut off (N), a wavelength control for putting the wavelength of the irradiating laser light away from the wavelength of the fluorescence light is performed. For example, when the photosensitizer to be used isin the second embodiment, the optimum wavelength (fundamental wavelength) is 664 nm if only treatment is to be performed. However, when diagnosis is to be performed concurrently with treatment, the wavelength of the laser light is shifted to 660 nm at which the excitation efficiency of the photosensitizer is not reduced so much (assuming that the excitation efficiency at the wavelength of 664 nm, i.e., the optimum wavelength is 1, the excitation efficiency is 0.9 at the wavelength of 660 nm). When diagnosis is performed in a manner as described above, the wavelength of the laser light is sometimes intentionally shifted from the fundamental wavelength optimum for treatment, and this is referred to as "fine tuning of wavelength". Therefore, according to this operation, in the case where the fine tuning of wavelength is effected in order to improve the signal-to-noise ratio S/N in fluorescence light separation when the setting of "performing diagnosis" is inputted from the input section 52, it is set at the input section 52 how is much degree the wavelength is shifted from the fundamental wavelength. The result is transmitted to the controlling device 8 in each laser unit 51a, 51b via the setting condition storage section 55, wavelength correcting section 56, and oscillation control section 57, so that the wavelength is changed.

Subsequently, in step S116, it is decided whether or not the wavelength of the irradiated laser light coincides with the set wavelength. The set wavelength has a range of tolerance. For example, when the photosensitizer to be used is NPe6, it has an absorption wavelength hand of 664±4 nm. Therefore, within this range, there is no substantial problem. (Therefore, if the wavelength is set to 660 nm in the fine tuning of wavelength in the case of diagnosis, the diagnosis can be achieved while performing treatment.) It is to be noted that, as described in connection with the first embodiment, the wavelength of the semiconductor laser has a temperature characteristic of 0.2 nm/deg, and therefore a wavelength accuracy of ±1 nm (corresponding to a temperature range of ±5° C.) can be sufficiently achieved in regard to the accuracy of temperature control. The current experimental apparatus has its tolerance of ±1 nm.

When the laser wavelength coincides with the set wavelength in step S116, the program flow terminates. Otherwise, when they do not coincide with each other, the program flow proceeds to step S117 to decide whether or not the wavelength control is performed within a limited time. The "limited time, is a limited time from a time when a wavelength of the irradiating laser light is set to a time when the wavelength is actually obtained. When the wavelength control is not completed within the limited time (temperature control in the embodiment), the control unit 7 decides that the temperature controlling device 8 (temperature control) of the laser unit 51a, 51b is failing, and then stops use of the laser unit.

It is to be noted that the wavelength control starts with the "turning-on of the power" of the entire apparatus toward the target of the default wavelength. Therefore, when especially no wavelength setting is performed after the power is turned on, the time point at which the power is turned on is the start point of the limited time.

The limited time depends on the capability of a temperature controlling device 8 of each laser unit. In time is set at five minutes. In one example, the limited time is set at five minutes. However, the time required for the cooling operation varies significantly depending on the output and the set wavelength of the laser.

The above-mentioned operation is controlled in the time measuring section 58, and when an abnormality (error) occurs, the occurrence of the abnormality is displayed for alarm in the displaying unit 10 via the oscillation control section 57, abnormality detecting means 62, and display control section .61.

When the wavelength control is not performed within the limited time in step S117, the program flow terminates in step S118 as the result of the occurrence of the abnormality. When the wavelength control is performed within the limited time, the program flow returns to step S116 to decide again whether or not the laser wavelength coincides with the set wavelength.

Figure 12:
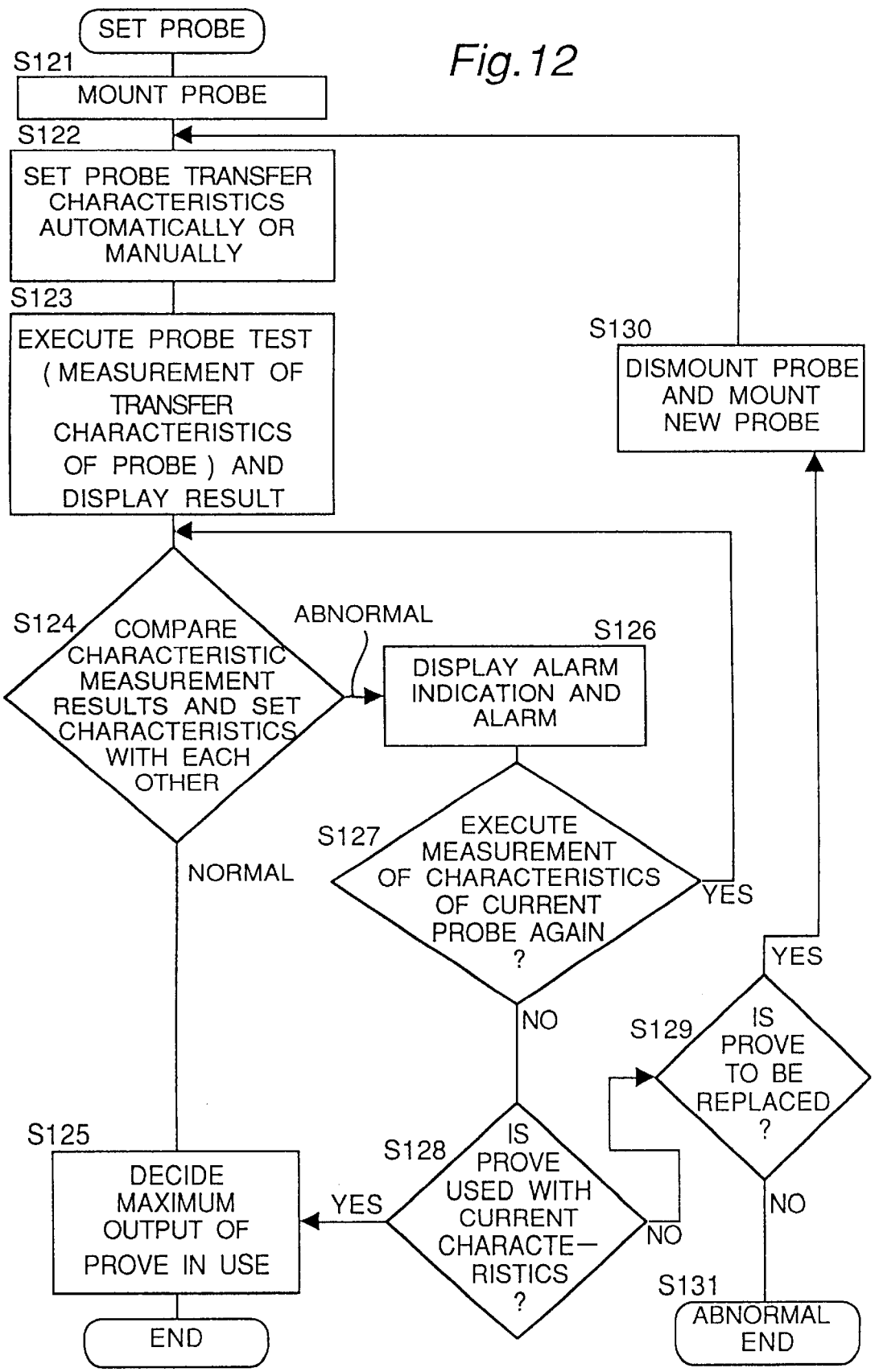
FIG. 12 is a flowchart showing a probe mounting step of FIG. 10.

FIG. 12 is a flowchart showing the probe mounting operation in step S12 of FIG. 10. According to this flowchart, mounting of the probe is performed in step S121. The probe may be mounted initially or immediately before the setting of the probe, meaning that the probe is permitted to be mounted any time before the setting of the probe. Configuration and intensity distribution of an irradiating beam of the laser light to the focus such as cancer vary depending on the type of the probe, and therefore an appropriate probe is to he selected according to the focus by a doctor.

Subsequently, the probe transfer characteristics are automatically or manually set in step S122. Thus, a is variety of probes is used at need. Taking a transfer efficiency of the laser light of the probe as an example, the transfer efficiency also varies depending on the type of the probe. In the case of a probe of an identical type, there is an inevitable variation in transfer efficiency due to a variation in manufacturing. However, the laser apparatus can only directly control the oscillation conditions of the semiconductor laser, and therefore the conditions (output, wavelength, energy quantity, intensity distribution and so forth) of laser light to be practically applied to the focus will vary every time the probe is changed unless a correction according to individual probe transfer characteristic is reflected on the control of the laser. In view of the above, setting and measuring of the probe transfer characteristics are performed in the present embodiment.

The setting of the probe transfer characteristics is, as described in the embodiment, effected when the probe is mounted to the laser apparatus. Practically, the setting is automatically effected by reading characteristic information (transfer efficiency, intensity distribution and so forth of laser light) of the probe recorded in the connector section of the probe by means of the connector 54 of the laser apparatus. When a probe of which characteristic information is not recorded is used, its is characteristic values can be manually set at the input section 52.

Then, a probe test, i.e., measurement of the transfer characteristics of the probe is executed in step S123, and the result is displayed.

By subsequently executing the probe test, it is inspected whether or not the probe transfer characteristics set as described above is actually obtained. Practically, by executing the probe test in a state in which the foremost end of the probe is inserted in the irradiating light characteristic measuring means 53, the oscillation control section 57 controls the laser units 51a and 51b in specified oscillation conditions to irradiate laser light, and the characteristics (output, wavelength, intensity distribution and so forth) of the laser light actually irradiated from the probe are measured by the irradiating light characteristic measuring means 53. The oscillation conditions in this case are transferred from the oscillation control section 57 to the abnormality detecting means 62, and the measurement results of the irradiating laser light characteristics are transferred to the abnormality detecting means 62 via the oscillation control section 57. The abnormality detecting means 62 decides whether or not an abnormality is occurring in the probe by calculating the probe transfer characteristics from the above-mentioned two sorts of information and comparing them with the probe transfer characteristics set as described hereinbefore. In other words, the abnormality detecting means 62 decides whether or not an abnormality is occurring in the probe by calculating the probe transfer characteristics from the laser oscillation conditions and the irradiating light characteristic measurement results and comparing the calculation results with the probe transfer characteristics set as described hereinbefore.

Then, in step S124, the characteristic measurement results and the set characteristics are compared with each other. When the measured characteristics are correct (normal), the program flow proceeds to step S125. When the characteristics are incorrect (abnormal), the program flow proceeds to step S126. In regard to the probe transfer characteristics, assuming that, for example, the transfer efficiency, which was 80% in the manufacturing stage, is 50% as the result of measurement of the present probe test, it can be considered that the transfer efficiency of the laser light is reduced due to breakage of the probe or smear of the foremost end of the probe or the like. Therefore,.an alarm indication is displayed in the displaying unit 10 via the display control section 61 in step S126 to proceed step S127.

In step S127, it is decided whether or not the measurement is executed again. When the measurement is executed again, the program flow returns to step S123, and the measurement is executed again to compare again the characteristic measurement results with the set characteristics in step S124. If it is required to measure again the probe transfer characteristics for the reason that an abnormality is occurring in the probe due to breakage of the probe or smear of the foremost end of the probe or the like, the probe test can be executed again. Otherwise, when the measurement is not executed again in step S127, the program flow proceeds to step S128 to decide whether or not the probe is used with the current characteristics. When the probe is used, the program flow proceeds to step S125. Only in the case where the probe cannot help being used in a deteriorated state for such a reason that no substitute probe is prepared regardless of the fact that the probe has an abnormality, "use of the probe with the current (deteriorated) characteristics" is to be selected. It is normally appropriate to replace the probe. The reason why such a mode is availed is to prepare for the case where treatment is required to be performed though the treatment efficiency is degraded (e.g., a longer time is required due to a lowered output).

When the current probe is not used in step S128, the program flow proceeds to step S129.

In step S125, a maximum output of the probe in use is decided. This decision is made in a manner as follows. For example, if the maximum output of the laser apparatus is 500 mW, the maximum output will be 250 mW when the transfer efficiency of the probe in use is 50%. Thus, the maximum output of the actual irradiating laser light to the affected part depends on the probe to be used. The maximum output intensity of the irradiating light is the maximum value of the output intensity of the irradiating light which can be set in the next item of "setting of output and energy quantity". The maximum output intensity of the irradiating light is calculated based on the transfer efficiency of the probe calculated in the stage of the probe test by the abnormality detecting means 62, and the maximum output intensity of the irradiating light is displayed in the displaying unit 10. After the maximum output is decided, the program flow terminates.

Otherwise, when the probe is not used with the current characteristics in step S128, the program flow proceeds co step S129 to decide whether or not the probe is to be replaced. When the probe is not replaced, the program flow abnormally terminates in step S131. When the probe is replaced in step S129, the program flow proceeds to step S130 to dismount the probe and mount a new probe. Thereafter, the program flow returns to step S122.

Figure 13:
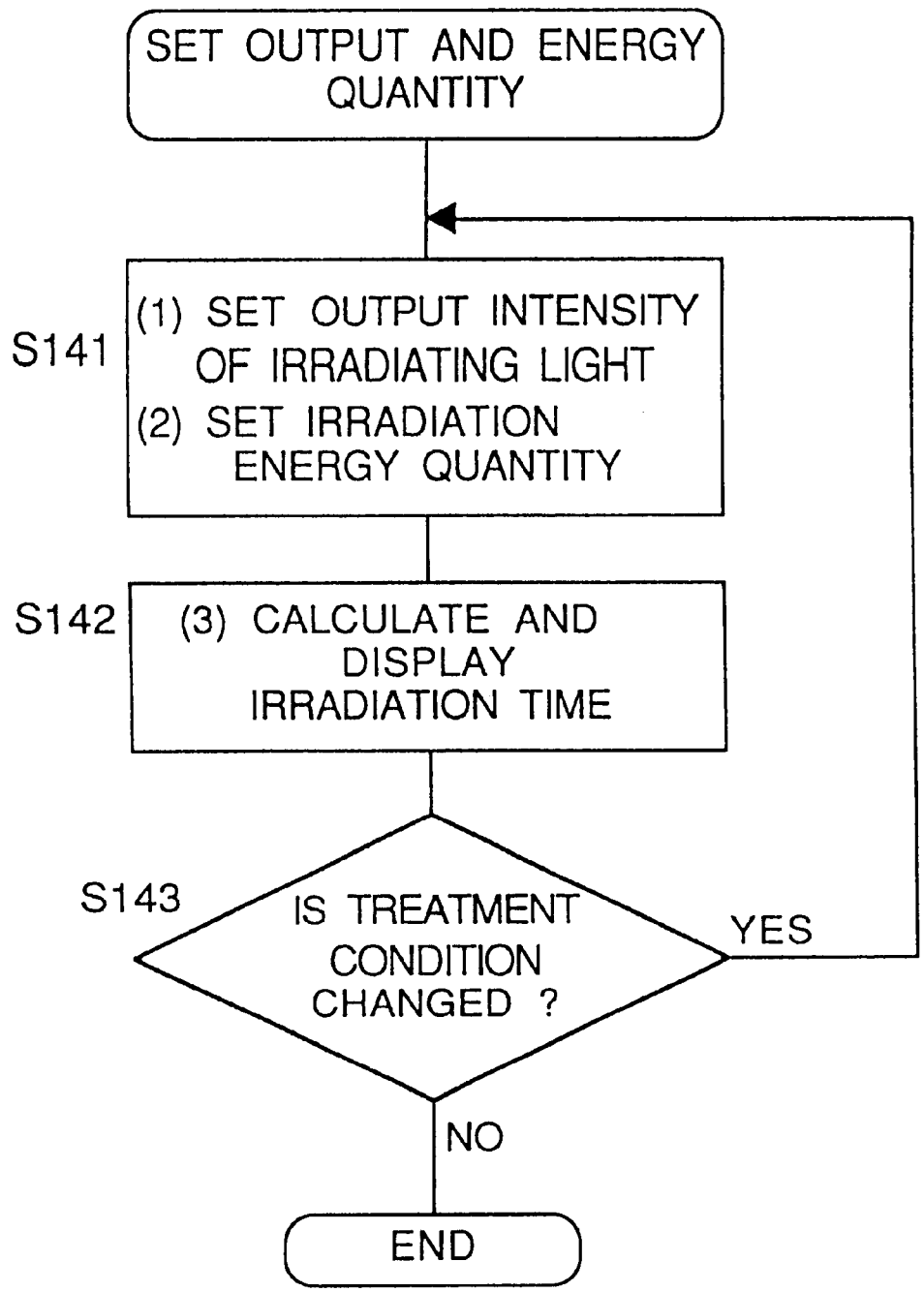
FIG. 13 is a flowchart showing an output and energy setting step of FIG. 10.

FIG. 13 is a flowchart showing the output and energy quantity setting operation in step S13 of FIG. 10. According to this flowchart, the output intensity of the irradiating light is set and the irradiation energy quantity is set in step S141. The setting of the output intensity of the irradiating light and the setting of the irradiation energy quantity can be performed independently at any time. The setting of these values influences calculation of an irradiating time in step S132. In regard to the "setting of the output intensity of the irradiating light and setting of the irradiation energy quantity", the output intensity of the irradiating light is set within a range below the maximum output intensity of the irradiating light set in step S125 in FIG. 12. Practical setting values of the output intensity of the irradiating light and the irradiation energy quantity are decided by the doctor according to treatment conditions. The setting is performed at the input section 52.

Subsequently, the irradiating time is calculated in step S142, and the result is displayed in the displaying unit 10. From the irradiation energy quantity and the output intensity of the irradiating light set as described above, the irradiating time is calculated by the energy quantity control section 59, and the result is displayed in the displaying unit 10 via the oscillation control section is 57 and the display control section 61. The calculation is executed according to the relation:

irradiation energy quantity [J]

=output intensity of the irradiating light [W]

x irradiating time [sec.]

For example, assuming that the output intensity of the irradiating light is set to 200 mW and the irradiation energy quantity is set to 200 J, then the irradiating time is calculated and displayed as:

200 J÷0.2 W=1000 sec.

Subsequently, it is decided whether or not the treatment condition is changed in step S143. When the treatment condition is changed, the program flow returns to step S141. When the treatment condition is not changed, the program flow terminates. This setting is just for the treatment conditions, and, therefore the necessity for the change is decided strictly by the doctor. As an example of the change, in order to reduce the irradiating time of 1000 seconds (=16 minutes and 40 seconds), the output intensity of the irradiating light is sometimes set to 400 mW (the irradiating time is 500 seconds) in the above-mentioned setting. It is to be noted that the change is effected by the doctor himself or herself when the maximum output intensity of the irradiating light is erroneously 400 mW and the doctor decides that the irradiation at 400 mW is causes no problem.

Figure 14:
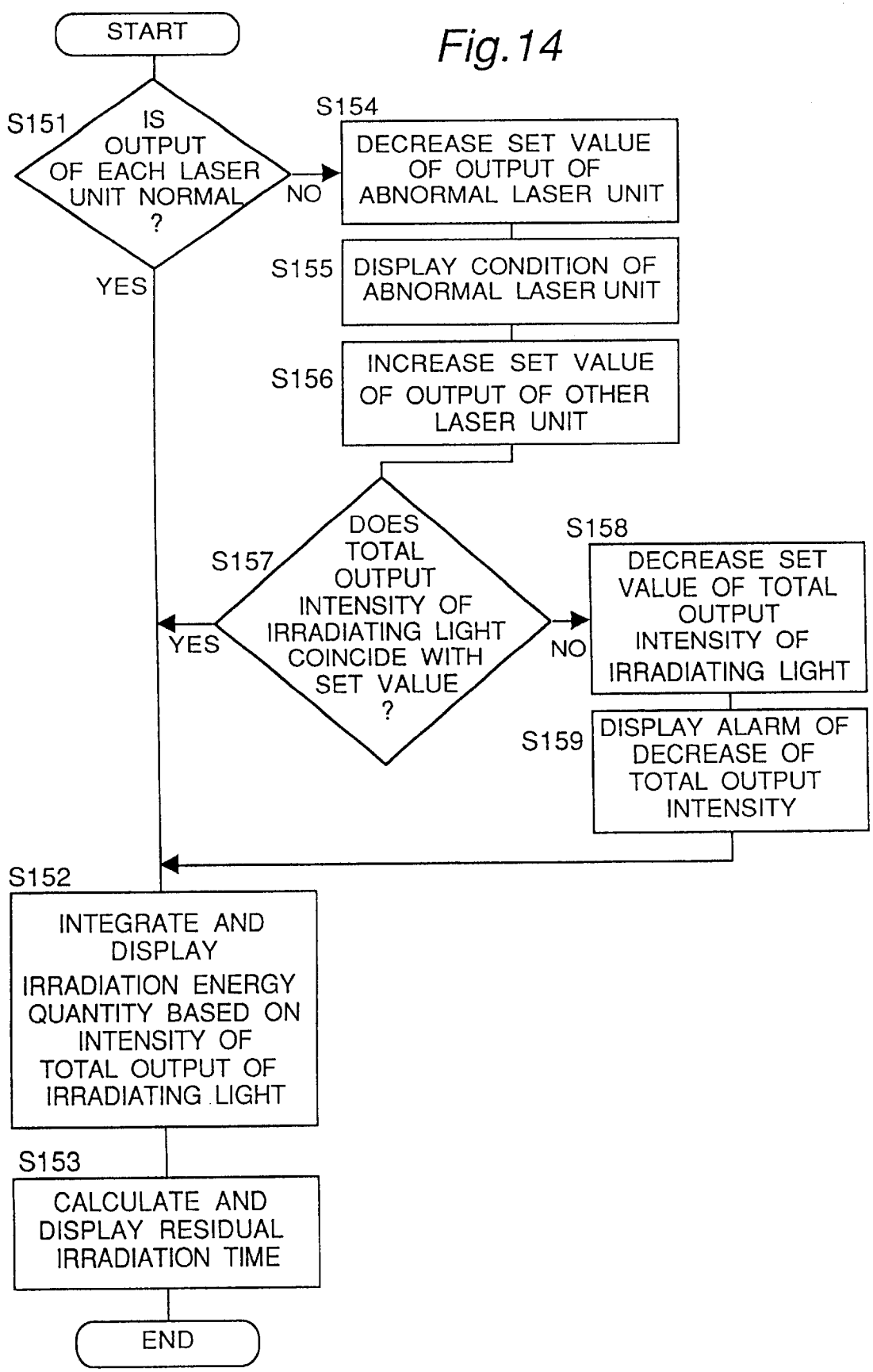
FIG. 14 is a flowchart showing control of irradiation energy quantity of FIG. B.

FIG. 14 is a flowchart showing the irradiation energy quantity control operation in step S4 of FIG. B. According to this flowchart, it is decided whether or not the output from each laser unit is correct (normal) in step S151. When the output is correct in step S151, the program flow proceeds to step S152 to integrate the irradiation energy quantity based on the total output of the irradiating light by the energy quantity control section 59 and then display it in the displaying unit 10. Thereafter, the residual irradiation time is calculated by the time measuring section 58 and then displayed in the displaying unit 10 in step S153 to terminate the program flow.

Otherwise, when the output is not correct in step S151, the program flow proceeds to step S154 to decrease the set output value of the abnormal laser unit. Then, the condition of the abnormal laser unit is displayed in the displaying unit 10 in step S155 and then the set output value of the other laser unit is increased in step S156 to make a decision whether or not the total output intensity of the irradiating light is coincided with the set value in step S157. When the total output intensity is coincided with the set value in step S157, the program flow proceeds to step S152. When the total output intensity is not coincided with the set value in step S157, the set value of the total output intensity of the irradiating light is decreased in step S158 and then the decrease of the total output intensity is displayed as an alarm indication in the displaying unit 10 in step S159 to proceed to step S152.

Operation of the diagnostic/treatment apparatus having the above-mentioned construction will be discussed with reference to the flowchart shown in FIG. 8. In step S1 of FIG. 8, firstly an operator such as a doctor sets the wavelength (step S11 of FIG. 10), energy quantity and irradiation intensity distribution of an irradiating light 85 for obtaining an optimum effect for treatment or diagnosis by putting into consideration the type and the excitation efficiency characteristic of the photosensitizer to be used, irradiating light permeability depending on the size, depth, and tissue components of the focus and so forth, and inputs the values from the input section 52 to the control unit 7 (steps S11 and S13 of FIG. 10, steps S111 through S115 of FIG. 11, and step S141 of FIG. 13). When a wavelength shifted from the optimum wavelength of the photosensitizer is used in a manner as described above and hereinafter or in a similar case, the type and the wavelength characteristic of excitation efficiency of the photosensitizer are additionally inputted. Further, transfer characteristics of transfer efficiency, irradiating light intensity distribution and so forth of a is laser probe 80 to be used are inputted (step S12 of FIG. 10).

The thus inputted setting values and the transfer characteristics of the laser probe 80 are stored in the setting condition storage section 55 (step S122 in FIG. 12). Among the setting values, the output intensity and the irradiating time for determining the irradiation energy quantity are corrected at need in a manner as described hereinafter by the wavelength correcting section 56 to decide irradiation conditions. Then, the control unit 7 oscillates beams of laser light 72a and 72b for a short time by the oscillation control section 57 with shutters 11a and 11bclosed (step S2 in FIG. 8), and then it is confirmed whether or not specified wavelength and output intensity are obtained according to detection results of the detecting units 9 of the semiconductor laser units 51a and 51b (steps S116 and S117 of FIG. 11). In this stage, when the required output intensity is not obtained, an irradiation energy quantity control for compensating for a fluctuation of output is effected by varying the irradiating time in a manner as described hereinafter in the stage of irradiation. Otherwise, when the set wavelength is not obtained, the fact is displayed for alarm to urge the operator to set again the irradiation conditions within a range of usable wavelengths. In this is stage, when a fluctuation of wavelength exceeding a permitted range or reduction of output intensity is detected, it is decided that an abnormality of laser is occurring, and stop of oscillation and display of an abnormality for alarm are effected (step S118 of FIG. 11).

Subsequently, when the probe test is selected at the input section 52 with the connector 54 of the laser probe 80 connected to the emission outlet 75 and with the foremost end portion 83 connected to the irradiation outlet of the irradiating light characteristic measuring means S3 (step S123 in FIG. 12), after confirming that the foremost end portion 83 is connected to the irradiating light characteristic measuring means 53, the control unit 7 emits laser light by opening the shutters 11a and 11b. In this stage, the measuring section of the irradiating light characteristic measuring means 53 measures the wavelength, total output intensity, and intensity distribution of the irradiating light 85 irradiated actually from the foremost end portion 83, and transmits the result to the control unit 7. The oscillation control section S7 of the control unit 7 calculates the transfer characteristics of the laser probe 80 from the measurement results of the irradiating light characteristic measuring means S3 and the output characteristic detection results of the detecting units 9 of the semiconductor laser units 51a and 51b.

Subsequently, during irradiation, the output of the emitted laser light is converted into an output of the irradiating light 85 by using the calculated values in the above-mentioned stage as transfer characteristic values of the laser probe 80, and the obtained value is transferred to the energy quantity control section 59 (step S125 of FIG. 12). The calculated transfer characteristics are further transmitted to the abnormality detecting means 62 together with the transfer characteristics of the laser probe 80 set initially to decide whether or not an abnormality such as deterioration is occurring in the laser probe 80 (step S124 of FIG. 12). When the abnormality detecting means 62 decides that an abnormality is occurring, the contents of the abnormality are transferred to the display control section 61 and displayed for alarm in the displaying unit 10 to urge the operator to replace the probe (step S129 of FIG. 12). Such a probe test is effected at need for output intensities and wavelengths in several steps. Further, the diagnostic/treatment apparatus of the present embodiment has inhibiting means for inhibiting the irradiation unless the probe test is once effected after the power is turned on.

Thus, the output characteristics of the semiconductor laser units 51a and 51b are controlled, so that the wavelength, total output intensity, and intensity distribution of the irradiating light 85 are controlled via the transfer characteristics of the laser probe 80 used.

The preparation for the irradiation of the diagnostic/treatment apparatus is thus completed through the aforementioned operations, thereby allowing the irradiating light 85 to start to be irradiated to the part to be treated. A control operation during irradiation will be discussed below.

During irradiation of the irradiating light 85 (steps S2 and S3 of. FIG. 8), the oscillation control section 57 controls the output characteristics of the semiconductor laser units 51a and 51b in a manner as described hereinbefore, so that the wavelength, total output intensity, and the intensity distribution of the irradiating light 85 are controlled via the actual transfer characteristics of the laser probe 80 used. Simultaneously with this control, the energy quantity control section 59 sequentially integrates the output intensity of the irradiating light 85 obtained through conversion as transmitted from the oscillation control section 57, as an energy quantity of irradiation which has been irradiated according to a time-measured signal of the time measuring section 58 (steps S4 and S7 of FIG. 8). Further, the integrated irradiation energy quantity is compared with the set value of the irradiation energy quantity to be irradiated set initially to calculate the remaining irradiation energy quantity and irradiating time to be required (step S142 of FIG. 13). During the above-mentioned time, the set values and the current values of the wavelength and the output-intensity of the sequentially irradiated light are transmitted, while the set values, the already irradiated portions, and the remaining portions of the irradiating time and the irradiation energy quantity are transmitted each from the display control section 61 to the displaying unit 10 to be displayed there. When an irradiation energy quantity equal to the set value is irradiated, the emission control section 60 closes the shutters 11a and 11b to complete the irradiation of the irradiating light 85, the fact that the operation has been normally terminated is displayed in the displaying unit 10, and the apparatus is put in a standby state (steps S5 and S8 of FIG. 8). It is to be noted that the operator can of course execute stopping of the irradiating operation even in the irradiation stage.

Next, the following will describe an operation of controlling the irradiation energy quantity of the irradiating light 85 when a fluctuation is occurring in the output of the laser light during irradiation. For example, when the output intensity of the laser unit 51a reduces, the oscillation control section 57 tries to increases the is input of the laser unit 51a to maintain the output intensity of the unit 51a. However, if the specified output intensity cannot be obtained (step S143 of FIG. 13), the oscillation control section 57 obtains the maximum output intensity that the laser unit 51a can obtain stably at a specified wavelength, and decides the maximum output intensity as the output intensity of the laser unit 51a. In this case, there is effected a compensation for a quantity corresponding to the reduction of the output intensity at the laser unit 51a by increasing the output intensity of the laser unit 51b to continue the irradiation. When the reduction of the output intensity at the laser unit 51a is so significant that no compensation therefor is effected by the laser unit 51b resulting in a shortage of the output intensity, the output intensity of the irradiating light reduces. However, by increasing the irradiating time, the initially set irradiation energy quantity is obtained. In this case, an alarm indicating the reduction of the output intensity is also displayed in the displaying unit 10 in addition to the aforementioned set value and the current value of the output intensity.

When the reduction of the output intensity is too significant or the output is unstable, the oscillation control section 57 stops the oscillation of the laser as the result of an abnormal failure. However, when the operator does not desire continuation of the irradiation at the reduced output intensity even if the reduction of the output intensity is within a permitted range, the irradiation can be of course stopped by the operator as described hereinbefore.

Next, the following will describe an operation of controlling the irradiation energy quantity of the irradiating light 85 when a laser light having a wavelength shifted from the optimum wavelength of the photosensitizer is used. Excitation is caused in the photosensitizer by the energy of the irradiating light 85, and an excitation efficiency depends on the wavelength of the irradiating light 85. As an example, a relationship between the excitation efficiency $\epsilon$ and the wavelength $\lambda$ in the case where a chlorin series NPe6 (trade name) is used as the photosensitizer is shown in FIG. 7 and, expressed by Equation 1:

$$\epsilon = f(\lambda)$$

where the excitation efficiency $\epsilon$ is normalized on the assumption that the excitation efficiency $\epsilon=1$ with respect to the irradiating light 85 having a wavelength $\lambda_0=664$ nm optimum for PDT.

Figure 7:
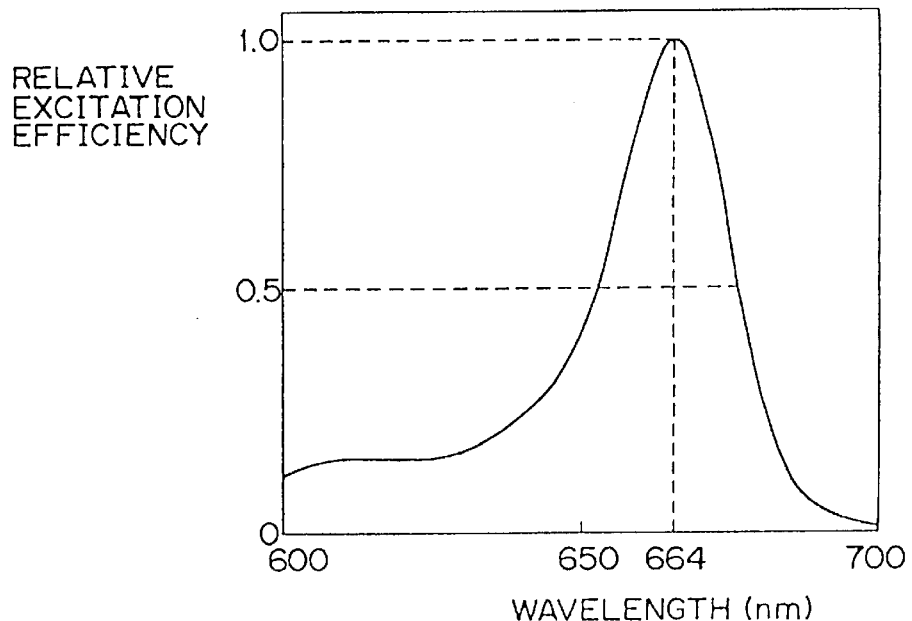
FIG. 7 is a graph showing a relationship between wavelength and excitation efficiency of an exemplified photosensitizer.

According to FIG. 7, for example, the excitation efficiency with respect to the irradiated light 85 having the wavelength $\lambda=652$ nm has a value of only 0.5. Even though the excitation efficiency is reduced as above, there is sometimes the case where an irradiating light 85 having a wavelength of 652 nm, which is shifted from the optimum wavelength of 664 nm, is used in order to obtain more clearly an image of fluorescence for diagnosing the part to be treated as described above. Furthermore, when the temperature control of the semiconductor laser units 51*a* and 51*b* is in a bad condition, it is inevitable to use the irradiating light 85 having a wavelength shifted from the optimum wavelength of 664 nm. In such a case, in order to obtain the same treatment effect as that achieved by PDT executed with an irradiation energy of 300 J at the wavelength of 664 nm of the irradiating light 85, there is required an irradiation energy of 600 J when the wavelength of the irradiating light 85 is 652 nm. Therefore, the output intensity of the irradiating light 85 is normally doubled. However, according to the present embodiment, paying attention to the irradiation energy quantity as described above, a control is achieved through correction so that the irradiation energy quantity, which is the time integral value of the output intensity, is doubled by increasing the irradiating time even if the output intensity of the irradiating light 85 cannot be doubled. Thus, when the irradiating light 85 having a wavelength $\lambda$ shifted from the optimum absorption wavelength is used, the wavelength correcting section 56 corrects a control target value of the irradiation energy quantity based on the excitation efficiency $\epsilon$ of the photosensitizer given by Equation 1 and decides the irradiation conditions.

Further, when a fluctuation of wavelength occurs in the irradiating light 85 during irradiation, the control target value of the irradiation energy quantity is corrected by the wavelength in the same manner as described above. The correction is applied to the remaining irradiation energy quantity calculated by the aforementioned energy quantity control section 59 at the point of time when the fluctuation of the wavelength occurs.

Next, a backup operation of the laser will be discussed. The diagnostic/treatment apparatus of the embodiment is provided with two semiconductor laser units 51*a* and 51*b* each being capable of obtaining a sufficient output as a light source. The total oscillation characteristic is controlled by individually controlling the semiconductor laser units 51*a* and 51*b* by the oscillation control section 57 of the control unit 7. With the above-mentioned operation, when, for example, the output intensity of the laser unit 51*a* is reduced, the total output intensity is maintained at a specified value by increasing the output intensity of the other laser unit is 51*b*. Further, when the laser unit 51*a* causes a failure and thus stops completely and the specified output intensity cannot be obtained singly by the laser unit 51*b*, the specified irradiation energy is obtained by increasing the irradiating time.

According to the embodiment as described above, in order to obtain the intended treatment effect of PDT, the control unit 7 comprised of the two semiconductor laser units 51*a* and 51*b*, irradiating light characteristic measuring means 53, setting condition storage section 55, wavelength correcting section 56, oscillation control section 57, time measuring section 58, energy quantity control section 59, emission control section 60, display control section 61, and abnormality detecting means 62 is provided paying attention to the irradiation energy quantity of the irradiating light 85 irradiated practically. With the above-mentioned arrangement, the actual transfer characteristics of the laser probe in use can be confirmed, by which the outputs of the emitted beams of laser light 72*a* and 72*b* can he converted into the output of the irradiating light 85, and the abnormality of the laser probe can be detected. Furthermore, even when the output intensity of one semiconductor laser unit 51*a* is reduced, compensation for the reduction can be effected by increasing the output intensity of the other semiconductor laser unit 51*b*. Furthermore, the irradiation energy quantity of the irradiating light 85 can be integrated and controlled, and therefore the irradiation energy quantity of the irradiating light 85 can be controlled so that it is maintained at the specified value by increasing the irradiating time when the total output intensity of the emitted laser light is reduced. Furthermore, when the irradiating light 85 having a wavelength shifted from the optimum wavelength of the photosensitizer is irradiated, an irradiation energy quantity capable of obtaining the intended treatment and/or diagnosis effect can be obtained.

The embodiment is provided with two semiconductor laser units. However, when a greater output intensity is required, or when a high reliability is required, three or more plural semiconductor laser units may be of course provided. When the plurality of semiconductor laser units are provided, they are still less bulky, less heavy, and less expensive than the excimer dye laser.

Furthermore, the transfer characteristics such as the transfer efficiency and irradiating light intensity distribution of the laser probe 80 to be used are inputted by the operator. However, it is possible to read the initial transfer characteristics of the laser probe 80 recorded at the connector 54 by the emission outlet 75 and then transfer them to the setting condition storage section 55 when the connector 54 of the laser probe 80 is connected to the emission outlet 75.

Furthermore, in regard to the correction of the control target value of the irradiation energy quantity depending on the fluctuation of the wavelength of the irradiating light 85, the control is executed based on the excitation efficiency characteristics with respect to the wavelength of the photosensitizer. However, it is acceptable to preliminarily calculate correction factor characteristics of the required irradiation energy quantity with respect to the wavelength according to Equation 1 and correct the control target value of the irradiation energy quantity based on the correction factor characteristics.

As described above, the present invention includes the irradiation energy quantity control means for the irradiating light, and by providing control means for executing control so that the irradiation energy quantity becomes a specified quantity, there can be implemented a diagnostic/treatment. apparatus capable of controlling to a specified value the energy quantity of the irradiating light that is irradiated from the foremost end portion of the laser probe and directly influences the treatment effect.

Furthermore, by providing the wavelength correction means for correcting the control target value of the irradiation energy quantity by the wavelength of the irradiating light, there can be implemented a diagnostic/treatment apparatus capable of obtaining an irradiation energy quantity which can achieve the same treatment effect as that achieved at the optimum absorption wavelength even when the wavelength of the irradiating light is shifted from the optimum absorption wavelength of the photosensitizer to be used.

Furthermore, by providing a plurality of laser units as light source and oscillation control means for controlling the total oscillation characteristics by controlling the plurality of laser units, individually controlling the plurality of laser units, there can be implemented a diagnostic/treatment apparatus obtaining a specified irradiation energy capable of obtaining a specified irradiation energy quantity even when an abnormality occurs partially in the light source.

Therefore, according to the present invention, the optimum control is multilaterally achieved to irradiate an irradiating light constantly having an appropriate energy, so that a superior diagnostic/treatment apparatus capable of executing exact diagnosis and effective treatment can be provided.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. A diagnostic/treatment apparatus for diagnosing and treating a focus in which a photosensitizer having an affinity to the focus has been preliminarily accumulated, said apparatus comprising:

a medical laser apparatus for irradiating the focus and including (a) a laser for irradiating laser light to the focus and having a variably controllable oscillating wavelength, wherein a full width at half maximum of the variably controllable oscillating wavelength is narrower than a width of an energy absorption band of the photosensitizer in which an energy absorption of the photosensitizer is at least 90% of a maximal energy absorption of the photosensitizer, and (b) a wavelength control means for controlling the oscillating wavelength of said laser to within the energy absorption band of the photosensitizer;

a light transmission line for guiding the laser light irradiated from said laser of said medical laser apparatus to a vicinity of the focus;

a image transmission line for guiding a fluorescence light emitted from the photosensitizer accumulated in the focus which has been excited by the laser light to observe the focus and a periphery thereof;

a fluorescence light extracting means for extracting only the fluorescence light transmitted in said image transmission line; and an image-pick-up/analyzing means for picking up and analyzing an image of the fluorescence light obtained by the fluorescence light extracting means.

2. The diagnostic/treatment apparatus as claimed in claim 1, further comprising an image display means for displaying an analyzed result of the image of the fluorescence light obtained by the image-pick-up/analyzing means, wherein the image of the fluorescence light is displayed by the image display means during treatment of the focus.

3. The diagnostic/treatment apparatus as claimed in claim 1, wherein the fluorescence light extracting means is a band-pass filter which passes the fluorescence light and blocks the laser light.

4. The diagnostic/treatment apparatus as claimed in claim 2, wherein the wavelength control means is for shifting the oscillating wavelength of the laser light away from a wavelength of the fluorescence light emitted from the photosensitizer and within the absorption band of the photosensitizer during treatment of the focus concurrently performed with diagnosis of the focus with the use of the displayed image of the fluorescence light.

5. A diagnostic/treatment apparatus as claimed in claim 3, wherein the photosensitizer having an affinity to the focus is a chlorine photosensitizer, and wherein the oscillating wavelength of said laser is variable and controllable within 664±5 nm, and wherein said band-pass filter passes a wavelength of 670 nm and blocks a wavelength of 660 nm.

6. A diagnostic/treatment apparatus as claimed in claim 3, wherein the photosensitizer having a affinity to the focus is a pheophorbide photosensitizer, and wherein the oscillating wavelength of the laser is variable and controllable within 650±10 nm, and wherein said band-pass filter passes a wavelength of 654 nm and blocks a wavelength of 644 nm.

* * * * *

UNITED STATES PATENT AND TRADEMARK OFFICE
CERTIFICATE OF CORRECTION

PATENT NO.     : 6,383,175 B1
DATED          : May 7, 2002
INVENTOR(S)    : Yoshiteru II et al.

It is certified that error appears in the above-identified patent and that said Letters Patent is hereby corrected as shown below:

<u>Title page,</u>
Item [56], References Cited, please insert the following below the last foreign patent document ("WO W09404665 12/1994"):

-- OTHER PUBLICATIONS
Programs and Abstracts of meeting of Japan Society for Laser Medicine, No. 14, issued October 8-10, 1993 to Y. II et al. "Developments of Semiconductor Laser Apparatus for PDT". --

Signed and Sealed this

First Day of October, 2002

*Attest:*

*Attesting Officer*

JAMES E. ROGAN
*Director of the United States Patent and Trademark Office*